(12) United States Patent
Bauer et al.

(10) Patent No.: US 6,534,315 B1
(45) Date of Patent: Mar. 18, 2003

(54) YEAST TRANSFORMATION CASSETTE

(75) Inventors: Jürgen Bauer, Thumeries (FR); Valérie Nacken, Marcq-en-Baroeul (FR); Annie Loiez, Lille (FR)

(73) Assignee: La Societe Lesaffre et Cie, Paris (FR)

( * ) Notice: Subject to any disclaimer, the term of this patent is extended or adjusted under 35 U.S.C. 154(b) by 0 days.

(21) Appl. No.: 09/415,216

(22) Filed: Oct. 12, 1999

(30) Foreign Application Priority Data

Oct. 9, 1998 (FR) .............................. 98 12702

(51) Int. Cl.$^7$ .............................. C12N 15/81; C12N 1/15
(52) U.S. Cl. ................. 435/483; 435/254.2; 435/320.1; 435/471; 435/477
(58) Field of Search ........................ 435/254.2, 254.21, 435/320.1, 471, 483, 463

(56) References Cited

U.S. PATENT DOCUMENTS 5,464,764 A * 11/1995 Capecchi et al.
5,637,504 A * 6/1997 Hinchliffe et al. ........ 435/320.1

FOREIGN PATENT DOCUMENTS

FR  2 615 527  11/1988

OTHER PUBLICATIONS

Rose et al. (in Goeddel et al., eds. 1990. Gene Expression Technology, Methods in Enzymology vol. 185, p. 254.*
Bernard. 1995. Gene 162: 159–160.*
Frankel et al. 1989. Molecular and Cellular Biology 9:415–420.*
New England Biolabs Catalog. copyrighe 1996. pp. 186–188 and p. 214.*
Hartzog et al. 1997. Current Opinion in Genetics and Development 7:192–198.*
Martinez–Garcia et al. 1996. Mol. Gen. Genet. 252:587–596.*
Smith, Julianne et al., "Methods in Molecular and Cellular Biology" vol. 5, *PCR–Based Gene Disruption in Saccharomyces cerevisiae*, pp. 270–277, (1995).
Alani Eric et al., "Genetics" vol. 116, *A Method for Gene Disruption That Allows Repeated Use of URA$^3$ Selection in the Construction of Multiply Disrupted Yeast Strains*, pp. 541–545, (1987).
Wach, Achim et al., "Yeast" vol. 10, *New Heterologous Modules for Classical or PCR–based Gene Disruptions in Saccharomyces cerevisiae*, pp. 1793–1808 (1994).

* cited by examiner

*Primary Examiner*—James Ketter
*Assistant Examiner*—Bronwen M. Loeb
(74) *Attorney, Agent, or Firm*—Foley & Lardner

(57) ABSTRACT

The present invention relates to a DNA cassette intended for the transformation of yeast, leaving no useless exogenous DNA but the gene(s) of interest comprising at least one negative dominant marker, two direct repeat sequences (DRS) which are non exogenous and non recombinogenic with the genome of the host strain, these two direct repeat sequences flanking the negative dominant marker and optionally at least one gene of interest containing, if necessary, the elements necessary for its expression in the host cell. The invention relates as well to a method of integration of gene(s) of interest or inactivation of a gene in yeast, and of transformation of yeast with the DNA cassette, and to yeast strains thus obtained.

45 Claims, 19 Drawing Sheets

GAP1, 464-478          TPS1, 1179-1203; Δ1194, Δ1197          TPK2, 745-768
TCACCACGTACGCTA        TATGAACTTGGTTTCTAGAATAT                TGGTCTCTAGGTGTTCTAATCTAC

5'-TCACCACGTACGCTA TAGAGACATAAAGCCAT TATGAACTTGGTTTCTAGAATAT TAGATCAAATAATGATGA TGGTCTCTAGGTGTTCTAATCTAC-3'

TAGAGACATAAAGCCAT                      TAGATCAAATAATGATGA
                       KSS1, 423-439                          POL2, 914-931

FIG. 1

SEQUENCE LISTING

<160> NUMBER OF SEQ ID NOS: 5

<210> SEQ ID NO 1
<211> LENGTH: 97
<212> TYPE: DNA
<213> ORGANISM: Saccharomyces cerevisiae

<400> SEQUENCE: 1
tcaccacgta cgctatagag acataaagcc attatgaact tggtttctag aatattagat      60
caaataatga tgatggtctc taggtgttct aatctac                              97

<210> SEQ ID NO 2
<211> LENGTH: 209
<212> TYPE: DNA
<213> ORGANISM: Saccharomyces cerevisiae

<400> SEQUENCE: 2
gtatctagac cattgaacac gacctaggaa gagattttt ttgacagcaa tctgggttca      60
aagaaactga catcgacttg ggatatctac gacctatggg ccaacagagt tgacaactcg     120
acagcgtctg ctatccttgg acggaataag acagccaccg gtattctcta caatgctacg     180
gagcaatcct acaaagacgg tttatctaa                                      209

<210> SEQ ID NO 3
<211> LENGTH: 43
<212> TYPE: DNA
<213> ORGANISM: Artificial Sequence
<220> FEATURE:
<221> NAME/KEY: misc_feature
<223> OTHER INFORMATION: primer

<400> SEQUENCE: 3
cgaattcggc gcgccgttta acatttaaa ttaattaagc tta                        43

<210> SEQ ID NO 4
<211> LENGTH: 51
<212> TYPE: DNA
<213> ORGANISM: Artificial Sequence
<220> FEATURE:
<221> NAME/KEY: misc_feature
<223> OTHER INFORMATION: primer

<400> SEQUENCE: 4
gatctaagct taattaattt aaatgttaa acggcgcgcc gaattcgagc t                51

<210> SEQ ID NO 5
<211> LENGTH: 35
<212> TYPE: DNA
<213> ORGANISM: Artificial Sequence
<220> FEATURE:
<221> NAME/KEY: misc_feature
<223> OTHER INFORMATION: primer

<400> SEQUENCE: 5
ccattgtttt aatgaggcgc gccgtttaaa ctcac                                35

YEAST TRANSFORMATION CASSETTE

The present invention relates to a yeast transformation tool or cassette family leaving in yeast no exogenous DNA fragment other than the fragments coding for proteins of interest.

The subject of the present invention is an integration-excision cassette which makes it possible to inactivate one or more alleles of a gene and/or to insert a new gene, leaving in the host strain only yeast DNA and possibly the new gene.

The present invention also relates to a high copy plasmid in yeast having no unnecessary or useless exogenous DNA fragment, i.e. no exogenous DNA that is not required for the yeast searched function.

The invention also relates to a method of transforming yeasts using the said tools or cassettes as well as the transformed strains obtained.

Improving the productivity and robustness of yeast strains is a constant concern to which recombinant DNA technologies may help to provide answers.

Gene replacement is a molecular biology technique which is frequently used in yeast. A DNA fragment is cloned into a vector and then it is introduced into the cell to be transformed. The DNA fragment integrates by homologous recombination into a targeted region of the recipient genome (Orr-Weaver T., Szostak J. and Rothstein R., 1981, Proc. Natl. Acad. Sci. USA, 78, pp. 6354–6358). However, the recombination event is rare in practice and only occurs in a few cells. Accordingly, selectable markers are inserted between the sequences bringing about the recombination in order to make it possible, after transformation, to isolate the cells where the integration of the DNA fragment occurred by identifying the markers corresponding, for example, to a resistance to an antibiotic. However, these selectable markers are difficult to eliminate, which has the disadvantage, on the one hand, of not being able to reuse the same marker for another transformation, and, on the other hand, of leaving in the host cell exogenous DNA fragments.

The problem is further complicated for the industrial strains of *Saccharomyces cerevisiae* which are distinguishable from the laboratory strains by the fact that they are both aneuploid and polyploid, that is to say that many genes are present in several copies: multiple copies in tandem, multiple copies dispersed in the genome, families of genes only slightly different in their sequence and for which no difference in activity has been detected such as the SUC gene for example (Olson M., 1991, Genome Structure and Organization, in *Saccharomyces cerevisiae* in the Molecular Biology of the Yeast Saccharomyces—Genome Dynamics, Protein Synthesis and Energetics; Ed. Broach, Jones, Pringle, CSHL Press, New York).

This particular ploidy makes any manipulation intended to inactivate a gene by disruption or deletion of its alleles difficult because it is necessary to inactivate all the copies of the gene, most often by repeating the inactivation operation.

The prototrophic character of industrial strains does not make it possible to use so-called "auxotrophic" markers and involves only the use of dominant markers in all the transformations, but in this case, it is necessary either to have several different markers, or to eliminate the marker after each transformation so as to be able to reuse it for a new transformation.

Another problem consists in the fact that to carry out any transformation at all the DNA construct used often contains DNA of non-yeast origin which is not always eliminated or not in its entirety. Foreign DNA therefore remains present in the genome of the yeast. However, for marketing in the food industry sector, it is important that the yeasts do not contain DNA not originating from strains belonging to the same genus, preferably to the same yeast species, with the sole possible exception of the part of a gene of interest encoding for a protein which is not naturally produced by the yeast strain, such as for example a xylanase, a malate permease, a malolactic enzyme, a lactate dehydrogenase.

In yeast, the integration of a gene of interest into a DNA fragment or target gene occurs according to the principle of homologous recombination. For that, an integration cassette contains a module comprising at least one yeast marker gene and the gene to be integrated, this module being flanked on either side by DNA fragments homologous to those of the ends of the targeted integration site. These fragments will be termed hereinafter "recombinogenic" because they will bring about double homologous recombination allowing the insertion of the cassette. These recombinogenic fragments will be called hereinafter RS (=Recombinogenic Sequence). After transforming the yeast with the cassette by appropriate methods, a homologous recombination between the recombinogenic sequences of the construct and the corresponding regions of the target gene results in the inactivation of the target gene caused by the simultaneous integration of the construct, that is to say the replacement of the target gene by the integration cassette.

This technique also applies to the inactivation of a gene, which may be a disruption/interruption or a deletion; in the case of a total deletion, the entire target gene is exchanged; in the case of a disruption/interruption, the sequence of the target gene is interrupted, and in general, it is accompanied by a larger or smaller deletion; accordingly, the terminology "total or partial deletion" is sometimes used to designate both the deletion and the disruption of a gene, which has the result of blocking or modifying its expression. In these two particular cases, the cassette to be inserted into the target gene may contain only the selectable marker flanked by the recombinogenic homologous fragments.

The problem then posed is that of eliminating the unnecessary exogenous fragments, in particular the markers thus introduced, whose presence is generally considered to be inopportune. For that, it is possible to use the "pop-out" or spontaneous excision phenomenon in yeast. It is an intrachromosomal recombination event between identical or similar sequences which can occur naturally. A DNA loop forms between two similar direct sequences, and is then ejected, leaving in place one of the two recombined sequences. The frequency of this phenomenon increasing with the degree of sequence identity, it is possible to promote the elimination of a DNA fragment, for example of a selectable marker, by placing it between two identical direct sequences, termed direct repeat sequences (DRS). Thus, the marker is excised while a direct repeat sequence is conserved.

For example, an article describes a molecular construct (pNKY51) which makes it possible to disrupt or to delete a yeast gene (E. Alani, L. Cao and N. Kleckner, "A method for gene disruption that allows repeated use of URA3 selection in the construction of multiply disrupted yeast strains", Genetics, 116, pp. 541–545, August 1987). The vector is an *Escherichia coli* plasmid containing the URA3 gene (marker) flanked by direct repeat sequences derived from the Salmonella histidine operon (hisG). This plasmid is digested in order to produce a module (hisG-URA3-hisG) which is then flanked on either side by recombinogenic homologous sequences of the target gene to be disrupted. The cassette thus produced is integrated into the target gene of a $Ura^{3\text{-}1}$ yeast, and the strains having integrated the cassette may be isolated by selecting the $Ura^+$ strains. After excising the cassette, the strains become $Ura^-$ again.

The construct is used to disrupt or delete the yeast TRP1, SPO13, HO, RAD50 and LEU2 genes. The multiple transformations are carried out either by crossing strains carrying one transformation each, or by a series of transformations with different disruption constructs and by repeated Ura+ and Ura3− selection cycles in a single strain.

One of the two Salmonella direct repeat sequences hisG remains in the genome after each transformation.

This method makes it possible to reuse the marker (auxotrophic marker) for a new transformation.

This same type of method is described in the document EP 635,574 for transforming bacteria, yeasts or fungi, the essential characteristic of the method being, in place of the URA3 marker, the use of another specific marker gene, the amdS gene. The marker in question seems to be interesting in the case of fungi strains, in particular Aspergillus; however the use of the system appears to be complex in yeasts.

The document EP 220,009 describes a method allowing the integration of total or partial deletion cassettes in yeast using the so-called "Cre-lox" excision system; this method, developed in animals, can also be used in yeasts; the sequences equivalent to the direct repeat sequences are, in this case, the so-called "lox" specific sequences and the excision of the DNA sequence between the two "lox" sequences is carried out in the presence of a "Cre" recombinase.

One of the disadvantages of this system is that one of the "lox" sequences which remains is an exogenous DNA from a bacteriophage.

The document EP 814,165 describes a system which makes it possible, here again, to excise a module containing a marker by the action of a specific enzymatic system on sensitive sequences, the system being very similar to the "Cre-lox" system, insofar as it uses a recombinase specific to the DRS.

The aim of the present invention is to provide yeast transformation cassettes leaving no useless exogenous DNA fragment, and having on the one hand at least one negative and dominant selectable marker; and on the other hand two direct repeat sequences (DRS) being not exogenous and not recombinogenic with the yeast genome, these 2 direct repeat sequences (DRS) being placed on both sides of the fragment containing the negative dominant marker. This dominant counter-selectable marker is preferably an inducible marker. These DNA cassettes, subject of the present invention, contain preferably a second selectable marker.

The DNA cassette subject of the present invention contains optionally at least one gene of interest, arid additionally if necessary, the elements required for its expression in the host cell, for example, any appropriate promoter, enhancer and/or terminator. Any exogenous (=heterologous) DNA for the yeast genome, other than that of the said gene(s) of interest, is considered as unnecessary or useless exogenous DNA.

One of the aims of the present invention is to provide an integration/excision cassette allowing the integration of a gene of interest and/or the inactivation of a gene of the host, capable of being used in yeasts, which solves the previous problems, in particular which makes it possible to obtain integrations free of exogenous DNA while leaving in place only the DNA of yeast belonging to the same genus and optionally a gene of interest. In the present description, "exogenous DNA" is understood to designate a DNA derived from a genus which is different: or more specifically from a species which is different, from the genus or from the species of the transformed yeast strain.

Accordingly, the present invention relates to a DNA cassette intended for the integration of a gene of interest or for the inactivation of a gene in yeasts, characterized in that it contains:

at least one negative dominant marker, preferably two dominant selectable markers: one positive marker and one negative marker;

two direct repeat sequences (DRS) which are non-exogenous and nonrecombinogenic with the genome of the host strain, these two direct repeat sequences flanking the selectable marker(s);

two recombinogenic DNA sequences (RS) corresponding to the desired insertion site in the yeast, flanking in 5' and 3' the abovementioned two direct repeat sequences;

optionally one (or several) gene(s) of interest containing, if necessary, the elements necessary for its expression in the host cell, placed between a DRS sequence and the adjacent recombinogenic DNA sequence (RS).

This integration/excision cassette allows the total or partial deletion of genes present in the genome of industrial yeast strains and optionally the simultaneous integration of a new gene without any foreign DNA fragments remaining in the genome of the strain thus transformed (apart from possibly the newly cloned gene if this is the case). Preferably, the said integration/excision cassette will be designed so as to make it possible to transform several alleles, or even all the alleles of a gene one after the other without the risk of seeing transformations reoccurring in principle at the same site. It is systematically checked that the transformation of all the alleles or of a determined number of them has indeed taken place. The transformation procedure may be repeated several times, by virtue of the use of at least one different recombinogenic sequence (RS) each time, the two RS sequences directing the integration of the cassette. Preferably, the two RS sequences will be changed as explained below; if only one is changed, it will be preferably the RS sequence chosen in 3' of the insertion site.

When the integration/excision cassette is intended for the integration of a gene of interest, this means that, after the excision, the gene of interest and a DRS sequence will remain, this set being flanked by two recombinogenic sequences; When the cassette is intended for the inactivation of the gene, this may involve the inactivation of a gene by total or partial deletion; in this case, only one DRS sequence flanked by two recombinogenic sequences remains. It is important, in a general way, that the DRS sequence is noncoding; indeed, situated in 3' of a recombinogenic sequence, it could be expressed. Noncoding sequence is understood to mean a sequence which is not translated in the form of a peptide.

A problem often encountered for the expression of one or several genes of interest at a sufficient level is the need for a high number of copies of the said gene(s) of interest including the elements allowing their expression. Another aim of the present invention is to provide a high copy or expression plasmid for yeast which is free from useless exogenous DNA, which can be obtained by means of a yeast-*E. coli* shuttle plasmid containing two direct repeat sequences (DRS), being non-exogenous and non-recombinogenic with the genome of the host strain.

This yeast—*E. coli* shuttle plasmid, preferably *S. cerevisiae*—*E. coli* relates also to the invention, its characteristics being that it contains:

at least a negative and dominant selectable marker, preferably two selectable markers, two non-exogenous and non recombinogenic direct repeat sequences (DRS), these two sequences separating two regions in the circular plasmid: on the one hand the yeast part intended to be kept in the host yeast and to allow the expression of the gene(s) of interest and on the other hand the part or region used for obtaining the shuttle plasmid and intended to be eliminated by excision.

Preferably, the region placed between the two direct repeat sequences and intended to be eliminated by excision contains:

an *E. coli* replication origin a selectable marker for *E. coli* the negative dominant marker, preferably inducible, i.e. a gene encoding for a compound which is toxic for yeast, the said gene being expressed under particular conditions of culture medium, corresponding to the induction.

The second region delimited by the two direct repeat sequences (DRS) and intended to become the yeast high copy expression plasmid contains:

a yeast 2 micron replication origin a selectable marker of yeast origin an expression system with at least one gene of interest.

Another aim of the invention is also to provide DNA cassette in the form of a yeast high copy plasmid which is obtainable after excision of the hereabove defined yeast—*E. coli* shuttle plasmid and which contains a DRS sequence being non-exogenous and non-recombinogenic with the genome of the host strain, a yeast 2 micron replication origin, a selectable marker of yeast origin, an expression system with at least one gene of interest.

These new cassettes according to the invention preferably contain two selectable markers, one of those always being thus a negative and preferably inducible dominant marker. A dominant marker for the purposes of the present invention being a marker for prototrophic cells (or non-auxotrophic cells with respect to the protein encoded by the marker) allowing, in a particular growth medium suitable for the marker, only the growth of the clones having the desired modification. This is also called direct selection. A dominant positive marker is a marker whose expression in the host cell ensures survival under certain particular conditions; in most cases, this will be a resistance marker, that is to say that when the corresponding marker is expressed, it allows the cell to be resistant, for example to antibiotics or to other toxic substances. A dominant negative marker is in contrast understood to designate in general a marker whose expression is toxic for the host cells under particular conditions. It may be in particular a marker made "inducible" encoding for a toxic product, such as for example the RTA (Ricin Toxin A) gene, placed under the control of an inducible promoter which is highly repressed by glucose. This inducible promoter may be, for example, a promoter of a GAL gene, or a hybrid promoter such as the GAL10-CYC1 promoter.

The article by Frankel et al., "Selection and characterization of ricin toxin A-chain mutations in *Saccharomyces cerevisiae*", Molecular and Cellular Biology, February 1989, pp. 415–420, describes a method of selecting mutants producing an inactive toxin after transformation with a DNA construct containing the gene encoding for the ricin toxin A polypeptide chain under the control of the GAL1 promoter and induction of the expression of this gene.

The use of an inducible gene encoding for a toxic product such as the polypeptide of the ricin toxin A chain according to the present invention is different, because this gene is used as a negative marker allowing a counterselection, that is to say a second selection of the strains transformed by the integration cassette or the high copy plasmid, object of the invention, but which have lost the excision module. Of course, it will be systematically checked that the survival of the transformed yeast cells in an inducible medium is due to the loss of the excision module and not to a mutation of the RTA gene or the gene encoding for another toxic protein, inactivating the toxin produced. This may be carried out for the strains transformed with the integration cassette, on the one hand, by sequencing the transformed zone and, on the other hand, by checking for the absence of any detectable fragment of the RTA gene within the genome of the transformed strain. Similar verifications can be carried out with respect to the loss of certain DNA fragments by the yeast high copy expression plasmids, which are also a subject of the invention.

Examples of positive and negative markers are given below in greater detail.

The presence of two dominant markers makes it possible to provide a system with a very high efficiency and it makes it possible to choose universal markers for yeasts giving an easy direct selection.

It will have been understood that the positive marker makes it possible to directly select the transformed cells and then, after culturing in an inducing medium, the negative marker makes it possible to directly select the cells whose excision module will have been eliminated by "pop-out" or excision.

The excision of the module containing the two markers in the integration/excision cassette is carried out by virtue of the presence of the direct repeat sequences (DRS) whose structure also constitutes one of the characteristic features of the present invention.

In the same way, the presence of two markers allows the system constituted by the yeast—*E. coli* shuttle plasmid to be highly efficient. It will have been understood that the dominant and inducible negative marker allows to select the cells containing only a yeast plasmid or yeast plasmids having excised the part used for the construction of the shuttle plasmid because of to the presence of direct repeat sequences (DRS), characteristic features of the present invention. In this construction, the excision eliminates the negative and preferably inducible dominant marker; whereas the positive marker of yeast origin, which is situated in the other region of the shuttle plasmid delimited by the 2 direct repeat sequences (DRS), is kept and used for keeping a selectable pressure for the maintenance in yeast cells of the yeast high copy expression plasmids, obtained after excision.

These DRS sequences will be preferably chosen from:

yeast mosaic sequences, preferably belonging to the genus Saccharomyces and more preferably *Saccharomyces cerevisiae*, or yeast DNA sequences not present in the host strain.

Yeast <<mosaic sequence>> is understood to designate a DNA sequence consisting of fragments coming from different DNA sequences of one or more yeast strains, belonging to the same species, or even to the same subspecies.

In order to ensure that the fragments in question lead to the formation of a nonrecombinogenic <<mosaic sequence>>, each of these fragments will preferably contain less than 30 bp, and the DRS sequence will contain from 80 to 300 bp so as to ensure the excision. The length of the fragments, namely of the order of 10 to 30 bp, does not allow them to play the role of recombinogenic fragments; on the other hand, the overall DRS sequence consisting of these different fragments allows recombination with an identical DRS, and therefore the excision of the DNA fragment between 2 identical DRS sequences. Preferably, a DRS sequence contains about 90 to 200 bp or 210 bp. After excision, one of the 2 DRS sequences remains in place in the genome; it is therefore necessary that this sequence consists of yeast DNA, that is to say of DNA belonging to the same genus and preferably to the same species of yeast.

As was indicated above, it is also possible to use, as DRS sequences, fragments of a yeast gene which is absent from the industrial yeast host strain to be transformed. For example, the *Saccharomyces cerevisiae* species is described as assimilating and fermenting melibiose in a variable manner depending on the strains. All the industrial strains of bakers' yeast are melibiose "minus", on the other hand most industrial strains of brewery yeast are melibiose "plus", whereas all these strains belong to the *Saccharomyces cerevisiae* species. The MEL1 gene is consequently a good candidate for providing the DRS sequences of a transformation cassette of an industrial strain of bakers' yeast. The MEL1 gene is described in Patent EP 241,044; it is a gene which encodes for the α-galactosidase enzyme which hydrolyses melibiose to galactose and glucose. This gene is absent from the industrial strains of bakers' yeast which, for this reason, are not capable of consuming the entire raffinose in molasses. In this case, it is possible to use longer DRS fragments, of the order of 200 bp or 210 bp for example, in order to facilitate the excision, but remembering that the DRS sequence remaining after excision should have been made noncoding by any appropriate means such as changing the reading frame or the introduction of stop codons for example.

As already indicated, the DRS sequences described above are flanked in the integration/excision cassette, in 3' and 5', by recombinogenic DNA sequences, that is to say which allow integration into the target gene by double homologous recombination and which are called RS sequences. These two DNA fragments are of course prepared from sequences chosen from the target gene which will then correspond to the sites specifically recognized for the homologous recombination. The choice of the RS sequences thus determines the site for insertion of the cassette.

When it is desired to successively integrate the same excision module with optionally a gene of interest into different alleles of the same family of genes, it is necessary to choose the recombinogenic sequences so that they do not become recombined in an allele already transformed.

To do this, successive integration/excision cassettes will be constructed which have at least one recombinogenic sequence which is no longer present in the previous recombined sites, preferably the recombinogenic sequence not present in the previously recombined site will be chosen in 3' of this site. For example, fragments will be chosen starting from the 3' end of the target gene for the recombination and then approaching the centre of the said target gene for each successive cassette. Preferably, the 2 RS sequences will be changed each time according to this applied technique by choosing different RS fragments starting from the two ends of the target site for the recombination in the different successive integration cassettes.

The integration marker may be any dominant positive marker, that is to say which allows the yeasts possessing it to survive a selection pressure. This will be preferably a resistance marker, that is to say a gene which confers on the strain resistance towards a toxic component. The use of an auxotrophic marker (gene necessary for growth on a medium lacking a nutritive component) shall be a preferred solution for the maintenance of yeast high copy expression plasmids. It is required that auxotrophic mutations had been introduced into the concerned industrial yeasts by targeted disruption or deletion, like those which have been made possible by the integration/excision cassette according to the present invention.

Among the dominant positive markers which may be used as marker for resistance to a toxic compound, there may be mentioned (the toxic compound being cited first):

Copper: the *Saccharomyces cerevisiae* CUP1 gene, which allows resistance to copper and to cadmium. Its use as dominant positive selectable marker has been shown in strains sensitive to copper (Henderson et al. 1985, Curr. Genet. 9, pp. 133–138; Pentilä0 et al. 1987 Curr. Genet. 12, pp. 413–420; Hottiger et al. 1995, Yeast, 11, pp. 1–14).

Cycloheximide: mutant alleles of the *Saccharomyces cerevisiae* ribosomal CYH2 gene allowing resistance to cycloheximide when they are present with the wild-type CYH2 gene (homozygosity does not confer resistance (Struhl et al. 1983, Gene. 26, pp. 231–242));

FK520: the MDR3 gene, orginating from the mouse, encoding the P-glycoprotein when it is expressed in *Saccharomyces cerevisiae* confers on it resistance to FK520 (an antifungal and immunosuppressive agent) (Raymond et al., 1994, Mol. Cell. Biol. 14, pp. 277–286);

Fluoroacetate: the dehH1 gene, derived from Moraxella sp. expressed in *Saccharomyces cerevisiae* allows resistance to fluoroacetate (van den Berg et al., 1997, Yeast, 13(6), pp. 551–559);

Fluorophenylalanine: the dominant ARO4-OFP allele, which is a mutation of a nucleotide of the *Saccharomyces cerevisiae* ARO4 gene, allows resistance to the p-fluoro-DL-phenylalanine, or o-fluoro-DL-phenylalanine, and tyrosine mixture (tyrosine makes it possible to suppress the inhibition of the expression of this gene). Its efficiency as a marker for resistance to an amino acid analogue has been shown on several industrial yeast strains (Shimura et al. 1993, Enzyme Microb. Technol. 15, pp. 874–876);

Formaldehyde: the *Saccharomyces cerevisiae* SFA1 gene, when it is overexpressed allows resistance to formaldehyde five to seven times higher compared with the corresponding wild-type strain. This gene was used as selectable marker of a multicopy plasmid (Wehner et al. 1993, Yeast, 9, pp. 783–785). One of the advantages of this marker is the low cost of the toxic molecule (van den Berg et al. 1997—Yeast, 13(6), pp. 551–559);

Geneticin: the KanMX module, which contains the coding sequence kan$^r$ derived from the *Escherichia coli* Tn903 transposon, fused with the transcriptional control sequences of the TEF gene of the filamentous fungus *Ashbya gossypii*, or with any other functional transcriptional terminator and promoter, confers on *Saccharomyces cerevisiae* resistance to geneticin (G418) (Wach et al. 1994, Yeast, 10, pp. 1793–1808, among the numerous users of this marker);

Glyphosate: the coding part of the *Escherichia coli* aroA gene, inserted between the *Saccharomyces cerevisiae* terminator and promoter sequences, allows therein resistance to glyphosate (Kunze et al. 1989, Curr. Genet. 15, pp. 91–98);

Hygromycin B: the hph gene, originating from an *Escherichia coli* plasmid, placed under the control of the promoter of the *Saccharomyces cerevisiae* CYC1 gene allows resistance to hygromycin B (Gritz and Davies 1983, Gene. 25, pp. 179–188);

Methotrexate: the Mdhfr gene, encoding a dihydrofolate reductase in mice, confers on *Saccharomyces cerevi-* siae resistance to methotrexate (Zhu et al. 1986, Gene. 50, pp. 225–237);

Phleomycin: the Tn5ble gene, derived from *Escherichia coli*, allows *Saccharomyces cerevisiae* to acquire resistance to phleomycin. This gene is generally used with the Saccharomyces cerevisiae CYC1 terminator and TEF1 promoter (Wenzel et al. 1992, Yeast, 8, pp. 667–668);

Sulfometuron: the SMR1-410 gene, mutant allele of the *Saccharomyces cerevisiae* ILV2 gene, allows resistance to the herbicide sulfometuron, in a dominant manner in diploid heterozygous strains (Xiao et al. 1990, Plasmid. 23, pp. 67–70). A new mutant allele was recently identified (Xie et al. 1996, FEMS Microbiol. Letters, 137, pp. 165–168).

As regards the second marker, namely the negative marker, that is to say the marker for counterselection, it will be, as was indicated above, in most cases a marker made "inducible" and encoding, under induction condition, for a molecule which is toxic for the yeast cell.

An advantageous marker for counterselection is the coding part of the RTA (Ricin Toxin A) gene, placed under the control of an inducible promoter which is both strong and highly repressed by glucose, such as for example the GAL10-CYC1 promoter and a PGK1t terminator. The principle of these constructions from a yeast promoter and terminator is to use a promoter and a terminator derived from different genes, so as to minimize the risks of undesirable recombination in the yeast genome.

Of course it is then checked by sequencing of the transformed region that the exogenous DNA is absent, that is to say that the excision indeed occurred as expected. The absence of any detectable fragment of one or both markers within the genome of the transformed strain is also checked by hybridization, more particularly, the absence of any detectable fragment of the counterselectable marker. In the case of construction of the high copy expression plasmid, the positive marker is kept, and consequently this positive marker must correspond to a non-exogenous or homologous DNA sequence.

Other counterselectable markers may also be chosen among genes that are homologous and heterologous to the yeast genome and whose conditional over-expression on a centromeric plasmid is toxic for the host yeast. For example:

ATL2, gene from *Arabidopsis thaliana*, coding for a zinc-finger protein (Martinez-Garcia et al. (1996) Gene isolation in *Arabidopsis thaliana* by conditional over-expression of cDNAs toxic to *Saccharomyces cerevisiae*: Identification of a novel early response zinc-finger gene. MGG, 252:587–596.)

DUO1, gene from *Saccharomyces cerevisiae*, coding for a spindle pole body protein (Hofmann et al. (1998) *Saccharomyces cerevisiae* Duo1p and Dam1p, novel proteins involved in mitotic spindle function. J. Cell. Bio., 143:1029–1040) ;

GIN11, gene from *Saccharomyces cerevisiae* coding for a subtelomeric protein (Kawahata et al. (1999) A positive selection for plasmid loss in *Saccharomyces cerevisiae* using galactose inducible growth inhibitory sequences. Yeast, 15:1–10)

GIN12/SPC42, gene from *Saccharomyces cerevisiae*, coding for a component of the spindle pole body (Akada et al. (1997) Screening and identification of yeast sequences that cause growth inhibition when over-expressed. MGG 254:267–274)

H1-1, gene from *Arabidopsis thaliana*, coding for a histone H1 (Martinez-Garcia et al. (1996) Gene isolation in *Arabidopsis thaliana* by conditional over-expression of cDNAs toxic to *Saccharomyces cerevisiae*: Identification of a novel early response zinc-finger gene. MGG, 252:587–596.)

TPK1, gene from *Saccharomyces cerevisiae*, coding for a cAMP dependent protein kinase (Liu, H. et al. (1992) Construction of a GAL1-regulated yeast cDNA expression library and its application to the identification of genes whose over-expression causes lethality in yeast. Genetics,132:665–673).

The *Saccharomyces cerevisiae* mosaic repeat sequences correspond, in general, to the construction of a sequence of about 100 base pairs consisting of gene fragments existing in principle in the host cell, each of these fragments being of a length such that it does not in principle allow any recombination event when they are present in a mosaic sequence. These sequences are constructed in a manner such that no peptide chain can be encoded, for example by virtue of the introduction of stop codons at the appropriate sites.

The mosaic sequences may be constructed from short gene fragments which are highly probably conserved in the different yeast strains and are situated in only slightly variable regions of these genes. These only slightly variable regions are determined by searching for homology with other gene libraries using the B.L.A.S.T.A. programme (Altschul et al., 1997, Nucleic Acids Res., 25, pp. 3389–3402). Intron sequences known to be highly variable should be avoided. Preferably, when the host strain belongs to the *Saccharomyces cerevisiae* species, the choice of the short fragments constituting the mosaic sequence is made based on the sequence of the *Saccharomyces cerevisiae* strain from the MIPS in Munich (Mewes et al., 1997, Nucleic Acids Res., 25, pp. 28–30). These fragments are also chosen so that the mosaic sequence possesses nonsense codons, stopping the translation in the 6 reading frames (3 direct reading frames and 3 reverse reading frames).

One of the essential characteristics of the excision module existing in the transformation cassette which is the subject of the present invention is that it can be used whichever the chosen integration site in the yeast genome (case of the integration/excision cassette) or whichever the gene(s) of interest to be expressed. This property is directly dependent on the choice of the restriction sites which make it possible to introduce the gene(s) of interest and the RS sequences into the transformation cassette. The presence of a specific restriction site in these DNA fragments to be introduced into the cassette excludes the said site from being used afterwards to construct the said integration/excision cassette. For the excision module to be easily used for any construction, it is necessary that it contains at each of its ends at least one restriction site whose frequency in the genome is as low as possible. One of the characteristics of the invention is that the excision module contains at least 3 rare sites at its ends arid preferably at least 5 rare restriction sites. A rare restriction site is a site which is recognized by a type II endonuclease recognizing an octanucleotide sequence or any restriction site having the same characteristic of rarity. To illustrate this notion of rare frequency, it is recalled that in a DNA sequence having a 50% A-T and 50% G-C composition, the frequency of the presence of a specific hexanucleotide is 1 per 4096 and of a specific octanucleotide is 1 per 65,536. For example, the excision module will have at its 5' end, the PacI, AscI and PmeI sites, and at its 3' end the FseI and SwaI sites.

The present invention also relates to a method of integrating a gene of interest or of inactivating a gene in a yeast, characterized in that:

a) the said yeast is transformed with the aid of a DNA construct consisting of the integration/excision cassette as described above, b) the yeasts having integrated the said cassette are selected by means of a positive marker, c) and then the yeasts in which the cassette has been excised by virtue of the DRS sequences are selected among these yeasts by searching for the yeasts lacking the negative marker.

More particularly, the invention relates to a method of integrating several copies or of inactivating different copies of a gene in a yeast, characterized in that the method described above is repeated with an integration/excision cassette which contains, for each repetition of the method, at least one different recombinogenic DNA sequence chosen such that each site containing an integration cannot, in principle, be the subject of a recombination with the next cassette.

The integration/excision cassettes optionally containing a gene of interest corresponding to the definitions given above may be constructed according to the customary methods used in the field by persons skilled in the art.

This is also true for the E. coli-yeast shuttle plasmid allowing to obtain, after excision of the E. coli sequences and the negative marker a high copy expression plasmid in the yeast, containing only as exogenous DNA, the exogenous DNA of interest. The principles of construction, the elements of this shuttle plasmid are the same than those here above described.

More particularly, the invention relates to a method of transformation of a auxotrophic yeast in order to obtain many copies of at least one gene of interest with a shuttle plasmid as described above of which the selectable marker or positive marker of yeast origin is a marker complementing the auxotrophy of the host yeast, characterised by:

the said auxotrophic yeast is transformed with the above mentioned shuttle plasmid.

yeast cells, which only contain plasmids, of which the part corresponding to the E. coli fragments and to the negative marker has been excised, are selected on a minimal medium, i.e. a medium which does not contain the element for which the yeast is auxotrophic, this minimal medium being chosen in order to induce the dominant negative marker located in the shuttle plasmid region containing this marker and the E. coli DNA fragments, both flanked by the two DRS sequences.

Among the methods of transformation which can be used for yeast strains, there may be mentioned in particular that proposed by Ito et al. (1983, J. Bacteriol., vol. 153, pp. 163–168), or by Klebe et al. (1983, Gene, vol. 25, pp. 333–341), or by Gysler et al., (1990, Biotechn. Techn., vol. 4, pp. 285–290).

Finally, the present invention relates to the yeasts transformed with a cassette according to the invention and obtained by a method as described above and which contains only yeast DNA, with the possible exception of the gene(s) encoding for a protein of interest, the DRS sequences being noncoding. If the cassette, according to the invention is used for inactivation of a gene family, the yeasts according to the present invention will be such that the desired number of copies, that is to say the desired number of alleles of the same family of genes, will have been inactivated by integration/excision with the aid of cassettes according to the present invention, or optionally the entire copies will have been inactivated, so as to choose the intensity with which a gene will be expressed. Similarly, if one of the cassettes according to the invention is used for the expression of one or several genes of interest, the desired number of copies for the said gene(s) may be obtained.

Among the yeasts which are most particularly advantageous according to the present invention, there may be mentioned the yeasts of the genus Saccharomyces and in particular Saccharomyces cerevisiae, in particular the industrial strains and more particularly those of bakers' yeasts.

BRIEF DESCRIPTION OF THE DRAWINGS

FIG. 1: Composition of a mosaic direct repeat sequence (SEQ ID NO: 1).

SEQUENCE LISTING

SEQ ID No. 1: the sequence SEQ ID No. 1 is the mosaic direct repeat sequence whose design is described in Example No. 1 of the present invention.

SEQ ID No. 2: the sequence SEQ ID No. 2 is the direct repeat sequence MEL used in Example No. 3 of the present invention.

SED ID No. 3 : linker sequence used in example 7 to introduce restriction sites.

SEQ ID No. 4 : second linker used in example 7.

EXAMPLES

Example 1
Composition of a So-called "Mosaic" Direct Repeat Sequence

The *Saccharomyces cerevisiae* nonheterologous, mosaic direct repeat sequence was designed according to the approach presented in the description, in this case it contains the following 5 coding sequences corresponding to a total of 97 base pairs (FIG. 1). The fragments are chosen so that the mosaic sequence possesses stop codons preventing translation in the 6 reading frames. The position of the DNA fragments chosen for the mosaic is given with reference to the codon for initiation of translation according to the MIPS (Munich Information Center for Protein Sequence) classification:

GAP1, bp 464–478, derived from the ORF of YKR039W, encoding for a membrane glycoprotein serving for the transport of amino acids, KSS1, bp 423–439, derived from the ORF of YGR040W, encoding a protein homologous to an MAP kinase, TPS1, bp 1179–1203, derived from the ORF of YBR126C, encoding trehalose-phosphate synthetase; two cytosine residues at position 1194 and 1197 are eliminated from this fragment so as to generate an XbaI restriction site, POL2, bp 914–931, derived from the ORF of YNL262W, encoding the large epsilon subunit of DNA polymerase, TPK2, bp 745–768, derived from the ORF of YPL203W, encoding a catalytic subunit of the cAMP dependent protein kinase.

The mosaic sequence resulting from the assembly of the fragments identified above is given as SEQUENCE ID No. 1.

The practical absence of homology between the *Saccharomyces cerevisiae* genome and the entire mosaic sequence presented in SEQUENCE ID No. 1 was checked with the aid of a conventional programme such as BLAST search version BLASTN 2.0.5 accessible on the Internet (reference Altschul et al., 1997, Nucleic Acids Res., vol. 25, pp. 3389–3402). It was demonstrated that no genomic sequence close to this mosaic sequence existed, that is to say that the degree of identity of the total mosaic sequence with any part of the genome is less than 25%, and therefore sufficiently low to exclude the possibility of a homologous recombination between a *Saccharomyces cerevisiae* DNA fragment and the mosaic sequence.

Example 2
Construction of an Excision Module with Mosaic Sequences

In this example, the two direct repeat sequences allowing the excision of the module by homologous recombination are the mosaic sequence defined in Example No. 1 above.

Figure 2:
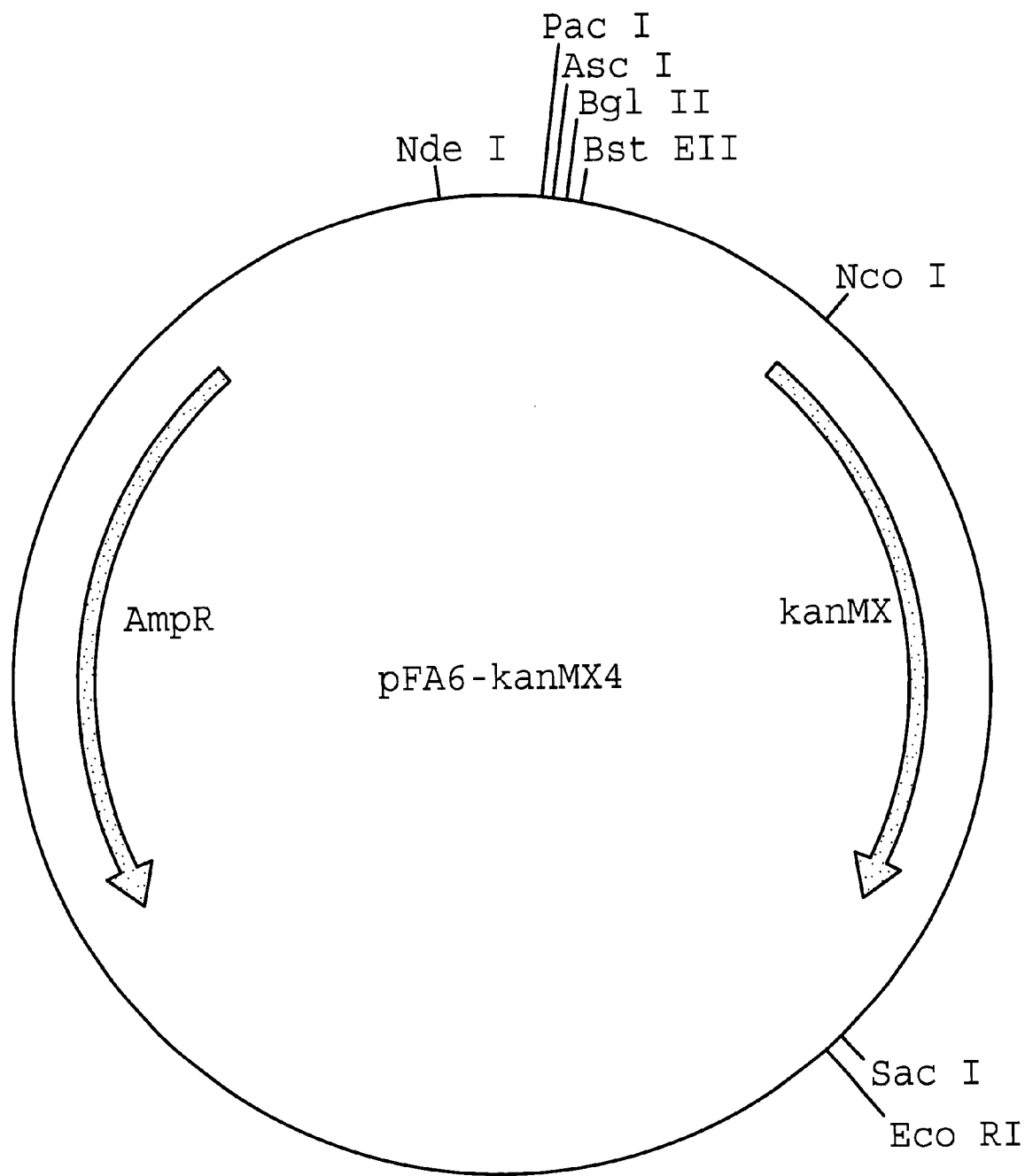
FIG. 2: Plasmid pFA6-kanMX4, carrying the dominant selectable marker kanMX and serving as base for the construction of an integration cassette.

The components of the excision module are constructed in the following order:

1) the plasmid pFA6-kanMX4 carrying the dominant selectable marker kanMX, serves as base for the construction (FIG. 2);

2) the mosaic direct repeat sequences are added separately to the plasmid pFA6-kanMX4, and then combined in a single plasmid;

3) the RTA suicide gene under the control of the promoter GAL10-CYC1 is inserted.

Each of these steps is preferably carried out in the following manner:

1) The marker kanMX is carried by the plasmid pFA6-kanMX4. This marker is composed of the coding part of the $kan^r$ gene conferring resistance to kanamycin, under the control of a promoter and of a terminator. The $kan^r$ gene, derived from the *Escherichia coli* Tn903 transposon, encodes an aminoglycoside phosphotransferase responsible for the resistance to kanamycin. The promoter and the terminator are the sequences for controlling the TEF (Translation Elongation Factor) gene of the filamentous fungus *Ashbya gossypii*. The construction of the plasmid pFA6-kanMX4 is described in detail in the article by Wach et al. (Yeast, 1994, 10, pp. 1793–1808) or in the manual Methods in Microbiology (vol. 26, Yeast Gene Analysis, chap. 5, pp. 67–81, ACADEMIC PRESS, ISBN 0-12-521526-6) It is also possible to use any promoter and terminator functioning in *Saccharomyces cerevisiae* and having a weak homology with the *Saccharomyces cerevisiae* promoters and terminators. Another solution for avoiding undesirable recombinations in *Saccharomyces cerevisiae* is to make a promoter and terminator combination derived from different genes of *Saccharomyces cerevisiae*, preferably the promoter and/or the terminator being hybrids such as the promoter GAL10-CYC1.

Figure 4:
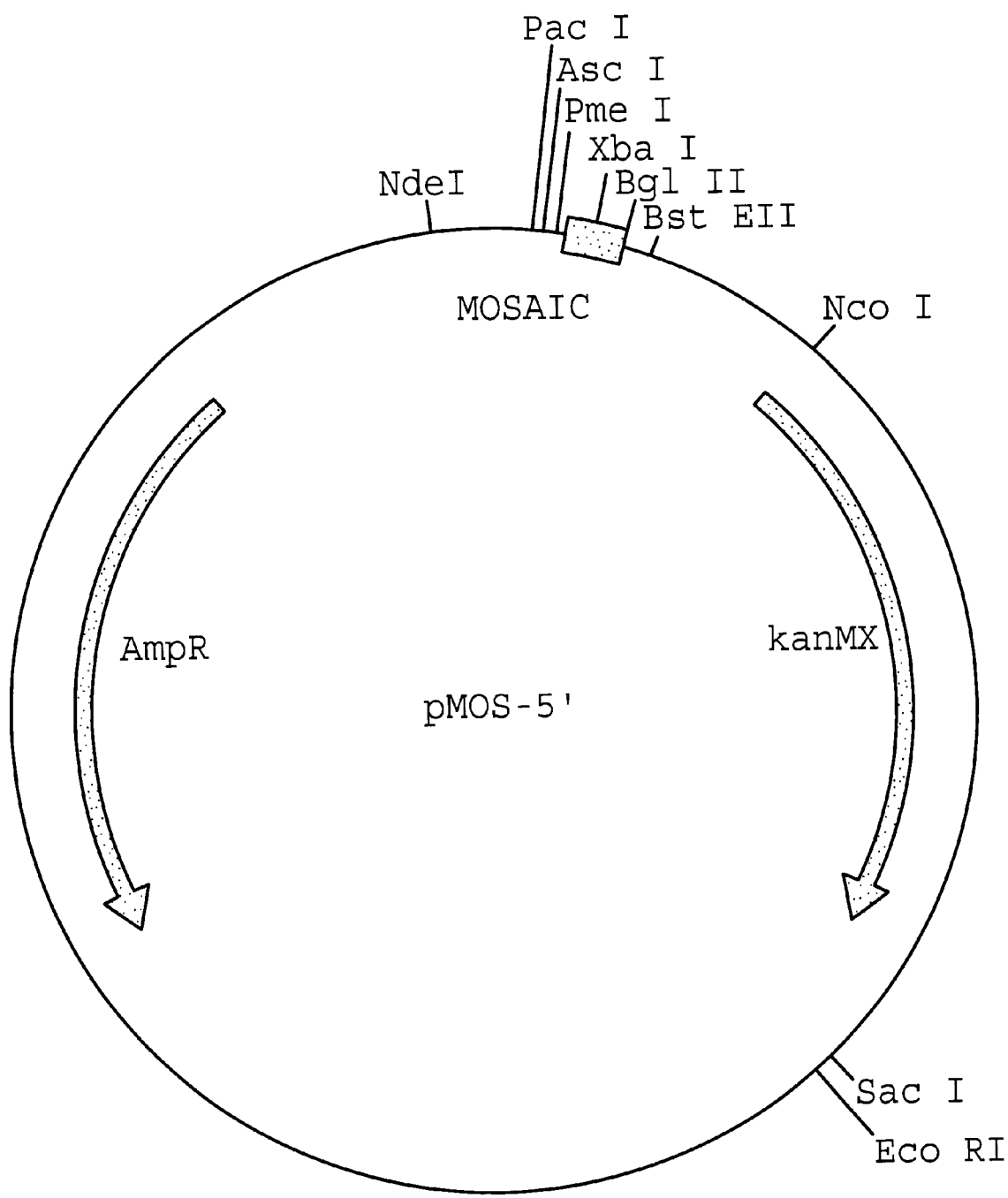
FIG. 4: Plasmid pMOS-5', resulting from the addition of a mosaic direct repeat sequence to the plasmid pFA6-kanMX4 in 5' of the kanMX marker.

2) The insertion into the plasmid pFA6-kanMX4 of the *Saccharomyces cerevisiae* mosaic sequences upstream and downsteam of the kanMX marker is carried out according to the following strategy illustrated by FIG. 3:

The mosaic sequence identified by the reference SEQ ID No. 1 is integrated on the 5' side of kanMX between the AscI and BglII restriction sites of the plasmid pFA6-kanMX4 giving an intermediate plasmid pMOS-5' (FIG. 4).

Figure 5:
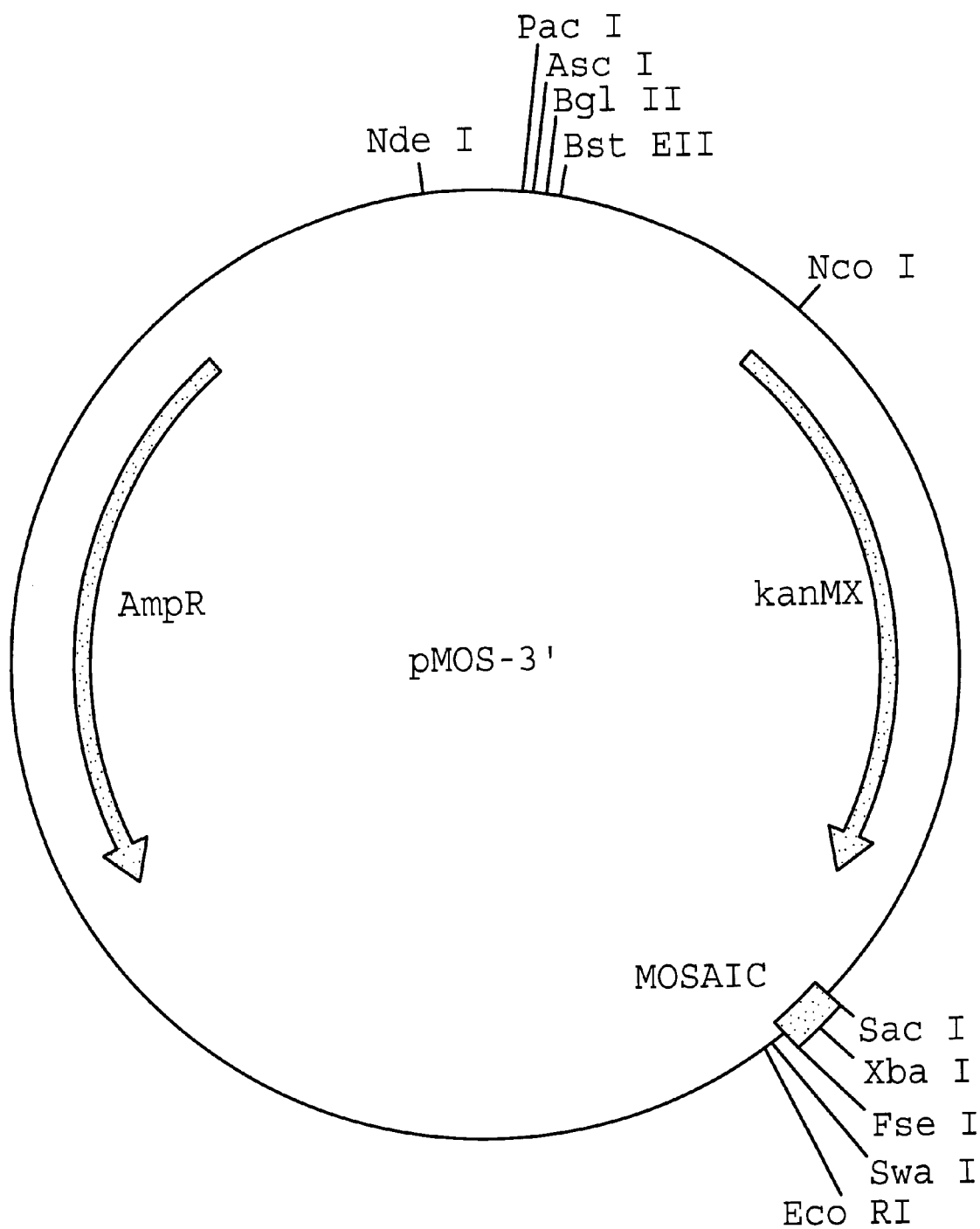
FIG. 5: Plasmid pMOS-3' resulting from the addition of a mosaic direct repeat sequence to the plasmid pFA6-kanMX4 in 3' of the kanMX marker.

In parallel, the mosaic sequence identified by the reference SEQ ID No. 1 is integrated on the 3' side of kanMX between the SacI and EcoRI restriction sites into the plasmid pFA6-kanMX4 giving an intermediate plasmid pMOS-3' (FIG. 5).

Figure 6:
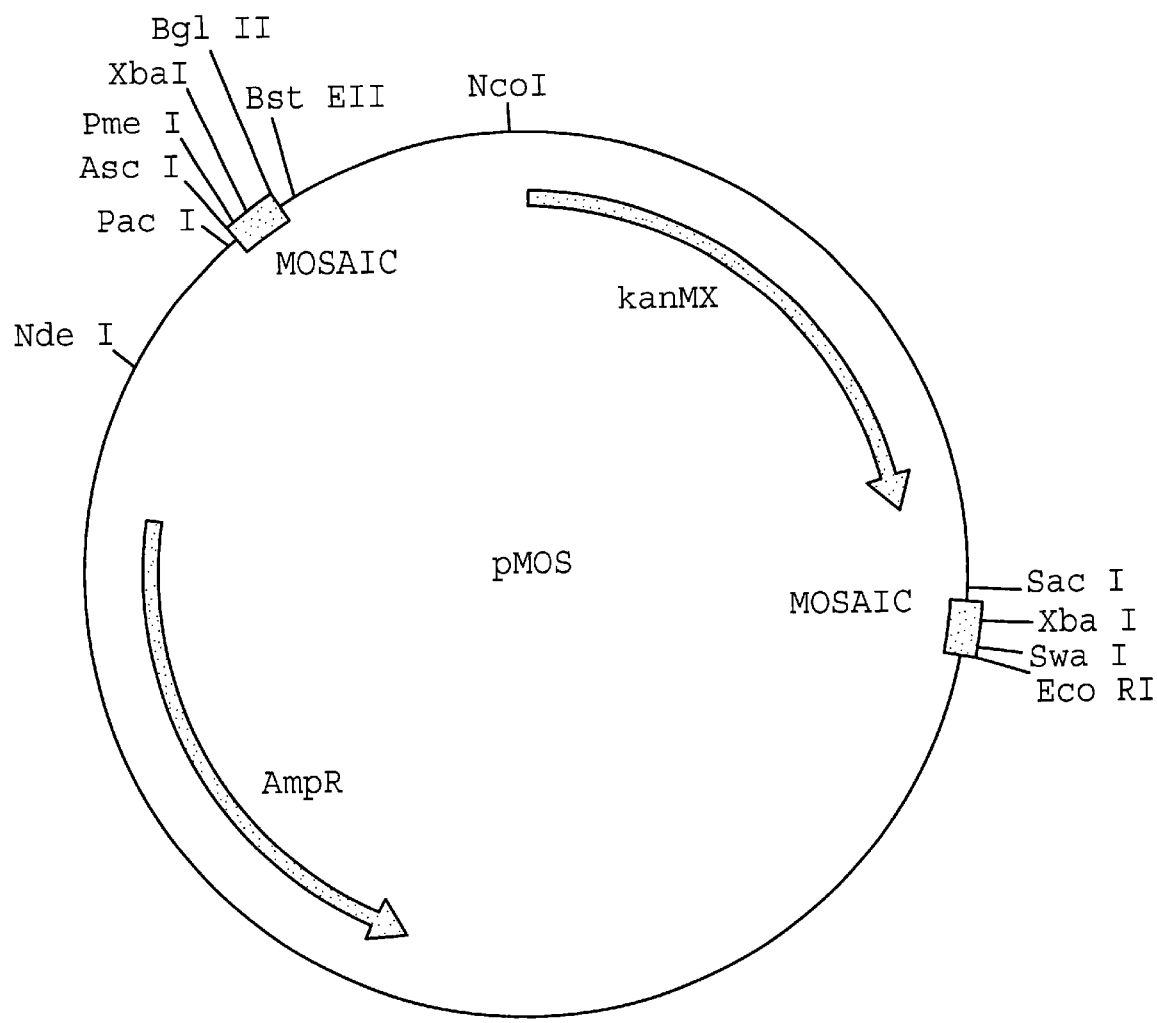
FIG. 6: Plasmid pMOS, resulting from the combination of the plasmid pMOS-5' and the plasmid pMOS-3', carrying the selectable marker kanMX and the two mosaic direct repeat sequences allowing the loss of the excision module by homologous recombination.

Next, these two plasmids are digested and linked so as to obtain the plasmid pMOS carrying the two mosaic sequences on either side of the kanMX marker (FIG. 6).

For the insertion of the mosaic sequence on the 5' side of kanMX (FIG. 3A), the plasmid pFA6-kanMX4 is amplified by reverse PCR (in a reverse PCR, it is the plasmid in its entirety which is amplified as template DNA). The fusion of the mosaic sequence with the plasmid is carried out with the aid of two primers L1 and L2 each composed of about 70 to 90 bases, namely about fifty bases of the mosaic sequence joined to a segment of about twenty bases intended to hybridize to the complementary sequence of pFA6-kanMX4.

In other words, the primer L1 is composed of the sequence complementary to the first approximately fifty bases of the mosaic sequence, corresponding to about half the said mosaic sequence and about twenty bases corresponding to the sequence of the plasmid in 5' of the point of insertion. The primer L2 is composed of the second approximately fifty bases corresponding to the second half of the mosaic sequence identified by the reference SEQ ID No. 1 and about twenty bases corresponding to the sequence of the plasmid in 3' of the point of insertion. The primer L1 contains, in addition, between the half mosaic sequence and the bases hybridizing to the plasmid, the sequence of the PmeI restriction site which will allow, where appropriate, the subsequent addition of a gene of interest specifically at the level of this site. These two primers L1 and L2 carry at their ends the XbaI restriction site defined in Example 1.

These two primers L1 and L2 are prepared by in vitro synthesis of oligonucleotides and purified. This synthesis of pure primers is carried out by specialist companies. Unless otherwise stated, all the primers defined below are obtained in the same manner.

The reverse PCR amplification of the plasmid pFA6-kanMX4 in the presence of the two primers L1 and L1 is carried out according to the recommendations of PCR Protocols, a Guide to Methods and Applications, M. A. Innis et al., Academic Press Inc., 1990, Part II, pp. 219–227.

This PCR reaction is catalysed by a thermophilic polymerase generating blunt ends, the said polymerase preferable lacking exonuclease activity, for example this enzyme may be VENT$_R$® (exo$^-$) DNA polymerase marketed by New England Biolabs, Inc., USA. The reaction medium is the conventional medium recommended by the supplier. VENT$_R$® (exo$^-$) is purified from a strain of *E. coli* that carries the VENT DNA Polymerase gene from the archaea *Thermococcus litoralis*. VENT$_R$® (exo$^-$) DNA Polymerase has been genetically engineered to eliminate the 3'→5' proofreading exonuclease activity associated with VENT$_R$® DNA Polymerase. This is the preferred form for high-temperature dideoxy sequencing reactions and for high yield primer extension reactions.

The samples obtained by PCR are then separated by migration on an agarose gel and the fragment corresponding to the desired DNA sequence is isolated and eluted with the aid of the Qiaquick kit (Qiagen GmbH, Germany) according to the protocol recommended by the manufacturer.

The purified fragment thus obtained is cyclized by an appropriate technique, in order to obtain a circular plasmid called pMOS-5' (FIG. 4). One method consists in causing cohesive ends to appear at the ends of the fragment obtained by PCR. For that, the XbaI restriction site present at the 5' end of each primer L1 and L2 is used. The PCR product obtained by amplification then contains this site at each end of the linear fragments. A digestion with the XbaI restriction enzyme leads to the creation of cohesive ends which promote the cyclization.

Figures 3A, 3B:
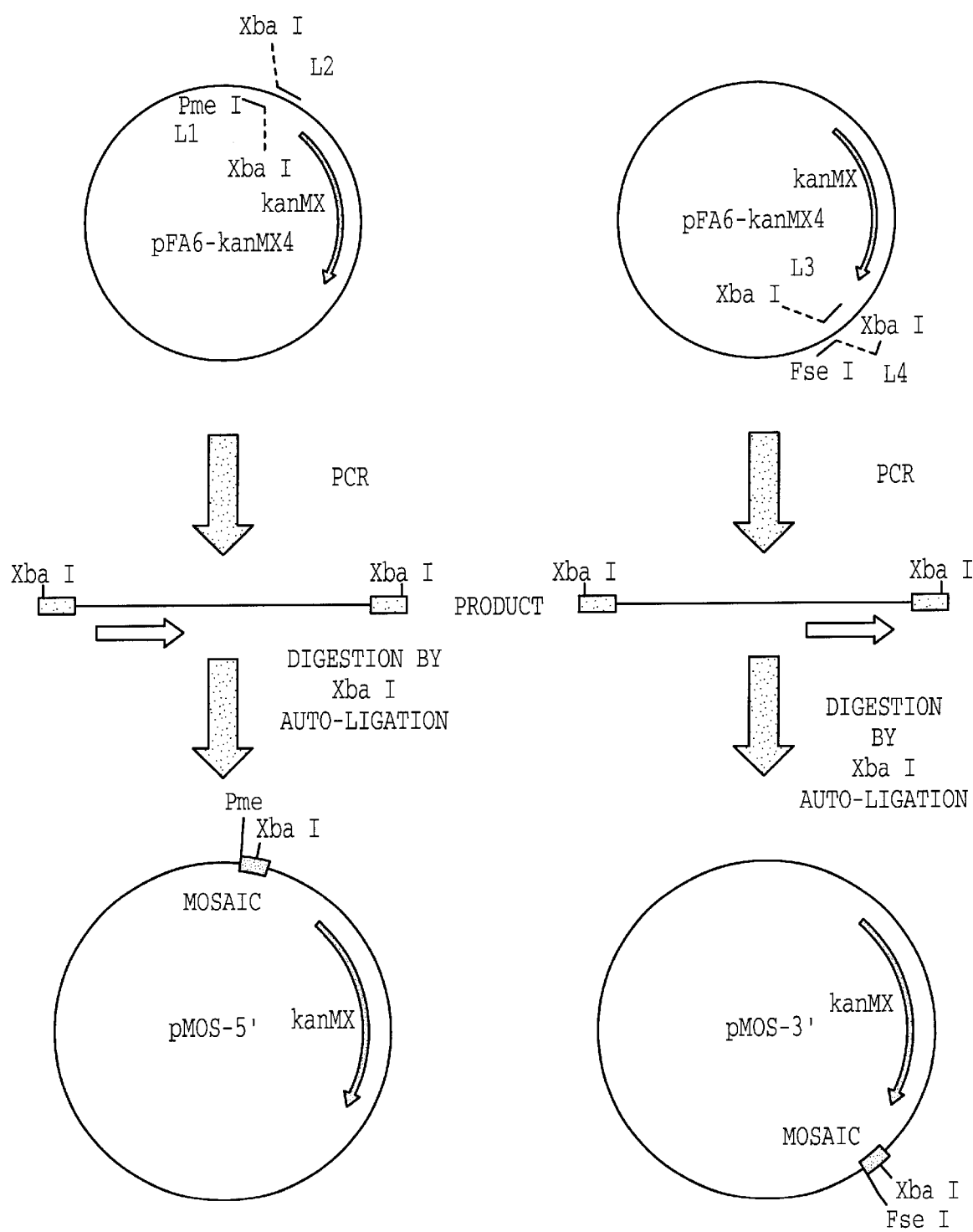
FIG. 3: Strategy for cloning two mosaic direct repeat sequences into the plasmid pFA6-kanMX4.

In parallel, the mosaic sequence is inserted into the plasmid pFA6-kanMX4 on the 3' side of the kanMX marker (FIG. 3B). The plasmid pFA6-kanMX4 is amplified by reverse PCR in the presence of two primers, L3 and L4. These primers each comprise half of the mosaic sequence corresponding to about fifty bases, linked to about twenty bases allowing hybridization in 5' and in 3' of the point of insertion between the SacI and EcoRI sites of the plasmid pFA6-kanMX4. The primers L3 and L4 are composed according to the same principle as the primers L1 and L2, that is to say that they contain respectively the sequence complementary to the first half and the second half of the mosaic sequence, that is to say about fifty bases each, and about twenty bases hybridizing to the plasmid, one downstream, the other upstream of the point of insertion. A restriction site which will allow subsequent integration of a recombinogenic sequence RS is in addition added to the primer L4. This restriction site, for example FseI, is inserted between the half mosaic sequence and the bases hybridizing to the plasmid. After amplification of the plasmid pFA6-kanMX4 in the presence of the primers L3 and L4 by reverse PCR according to techniques already cited for the primers L1 and L2, the PCR product is purified and then cyclized by an appropriate method, for example that proposed above for the cyclization of pMOS-5'. The restriction site SwaI is then introduced between, on the one hand, the EcoRI site present in the plasmid and, on the other hand, the FseI site carried by the mosaic sequence, by means of a linker carrying the SwaI site in its centre surrounded by EcoRI and FseI cohesive ends.

The plasmid resulting from all these constructions is called pMOS-3' (FIG. 5).

Finally, the plasmids pMOS-3' and pMOS-5' are digested with appropriate enzymes, for example with the endonucleases NdeI and NcoI, and both complementary fragments containing a mosaic sequence are ligated. The resulting plasmid is linearized by the BamHI restriction endonuclease, treated by the Mung Bean Nuclease (New England Biolabs, UK) and self-ligated to eliminate the BamHI restriction site, resulting in the plasmid pMOS (FIG. 6). This plasmid contains a complete mosaic sequence on each side of the kanMX marker.

The two mosaic repeat sequences carried by pMOS are the sequence designated by the reference SEQ ID No. 1.

The plasmid pMOS contains 5 rare restriction sites, namely the PmeI, FseI and SwaI sites provided in the context of the constructions described above, plus two rare sites namely PacI and AscI initially carried by the plasmid pFA6-kanMX4 which was used as starting material, by way of example, for the constructions. Of course, if the necessary rare sites are not present in the starting plasmid, they can be added with the aid of a linker.

Figure 7:
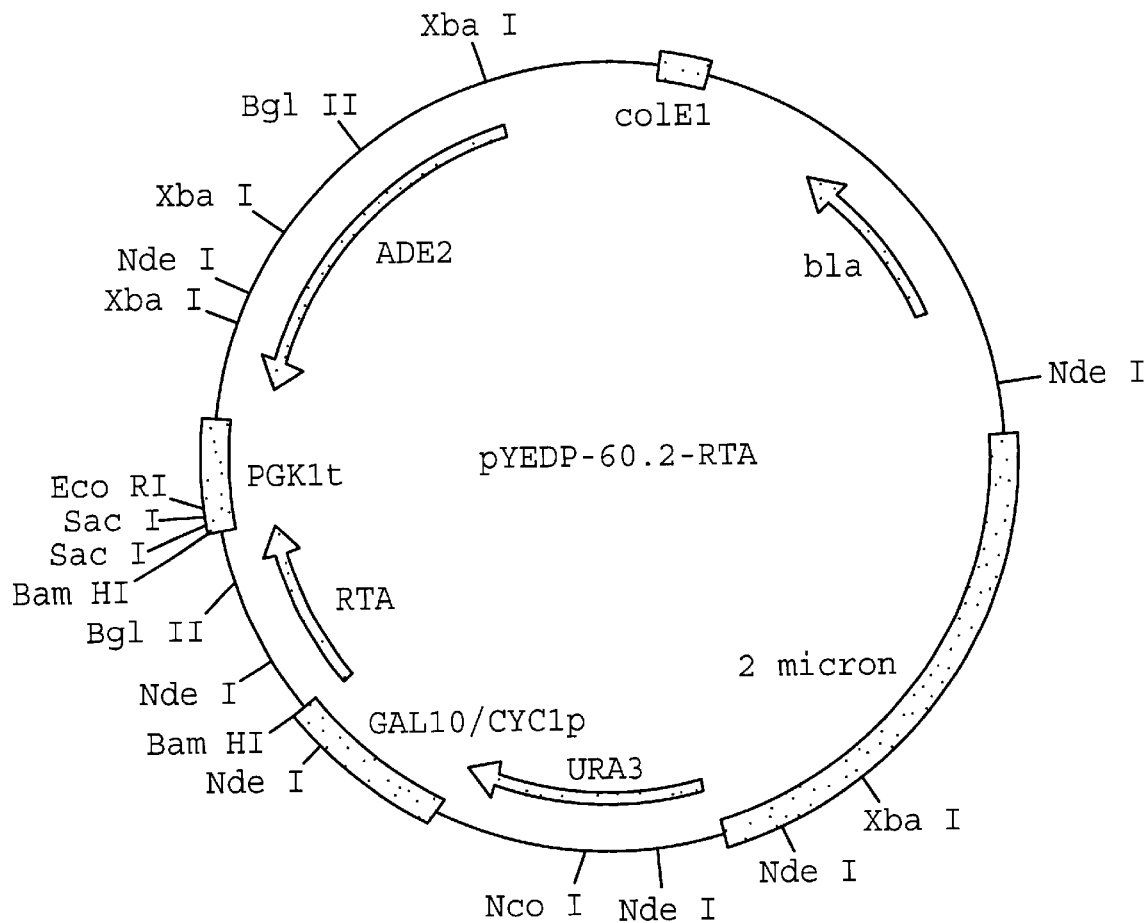
FIG. 7: Plasmid pYEDP-60.2-RTA, carrying the RTA suicide module to be integrated into the plasmid pMOS and which will act as negative selectable marker in the integration cassette.

3) Introduction of the RTA suicide module into the excision module carried by the plasmid pMOS:

The RTA suicide module is carried by the plasmid pYEDP-60.2-RTA described in FIG. 7 and deposited under the terms of the Treaty of Budapest in the *Escherichia coli* strain DH5α[YEDP-60.2-RTA] at the Collection Nationale de Culture de Micro-organisms, C.N.C.M., Institut Pasteur, 25 rue du Docteur Roux, 75724 Paris cedex 15, under No. I-2083 on Oct. 1st 1998. This suicide module is composed:

of the coding part of a gene encoding a compound which is toxic for the yeast of a *Saccharomyces cerevisiae* inducible hybrid promoter, this hybrid promoter having been chosen for its strong promoter characteristics, practically inactive outside the induction medium, which allows the strains not to be impeded in their growth by a residual activity of the promoter. The hybrid promoter GAL10-CYC1 is described in the article by L. Guarente et al., 1982, Proc. Natl. Acad. Sci. USA, vol. 79, pp. 7410–7414.

of a terminator derived from another *Saccharomyces cerevisiae* gene.

Such a construction has the merit of minimizing the risks of undesirable recombination.

The plasmid pYEDP-60.2-RTA is then used to introduce the RTA suicide module at the level of the BstEII restriction site of the plasmid pMOS, a site which is initially present in the plasmid pFA6-kanMX4. To do this, the RTA suicide module is amplified by PCR using the plasmid pYEDP-60.2-RTA as template and in the presence of the primers L5 and L6. The primers L5 and L6 are designed so as to introduce BstEII restriction sites at the two ends of the RTA suicide module. The PCR reaction is carried out according to the conventional techniques described by Sambrook et al., (Molecular Cloning, a Laboratory Manual, Cold Spring Harbor Laboratory Press, 1989, vol. 2, pp. 14.01–14.35).

Figure 8:
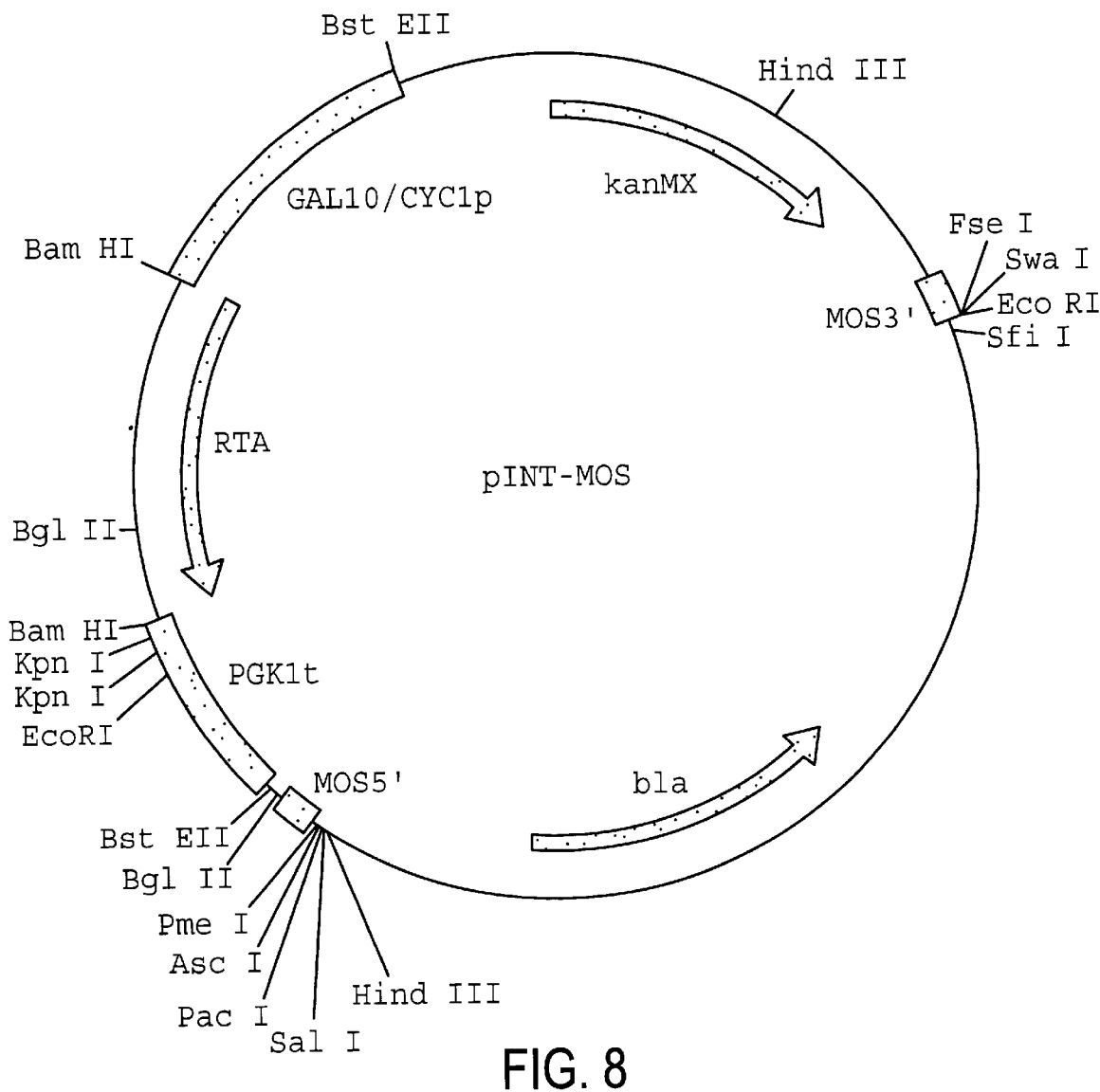
FIG. 8: Plasmid pINT-MOS, carrying the so-called "excision module" central part of the integration cassette.

Likewise, the PCR amplifications of the different fragments used in the present invention are carried out, unless otherwise stated, according to the recommendations of this manual. After digestion with the BstEII enzyme, the RTA suicide module is inserted into the plasmid pMOS, previously linearized by digestion with BstEII. The plasmid thus obtained is called pINT-MOS (FIG. 8).

4) Replacement of the RTA suicide gene carried by the pINT-MOS by the H1-1 gene.

Figure 13:
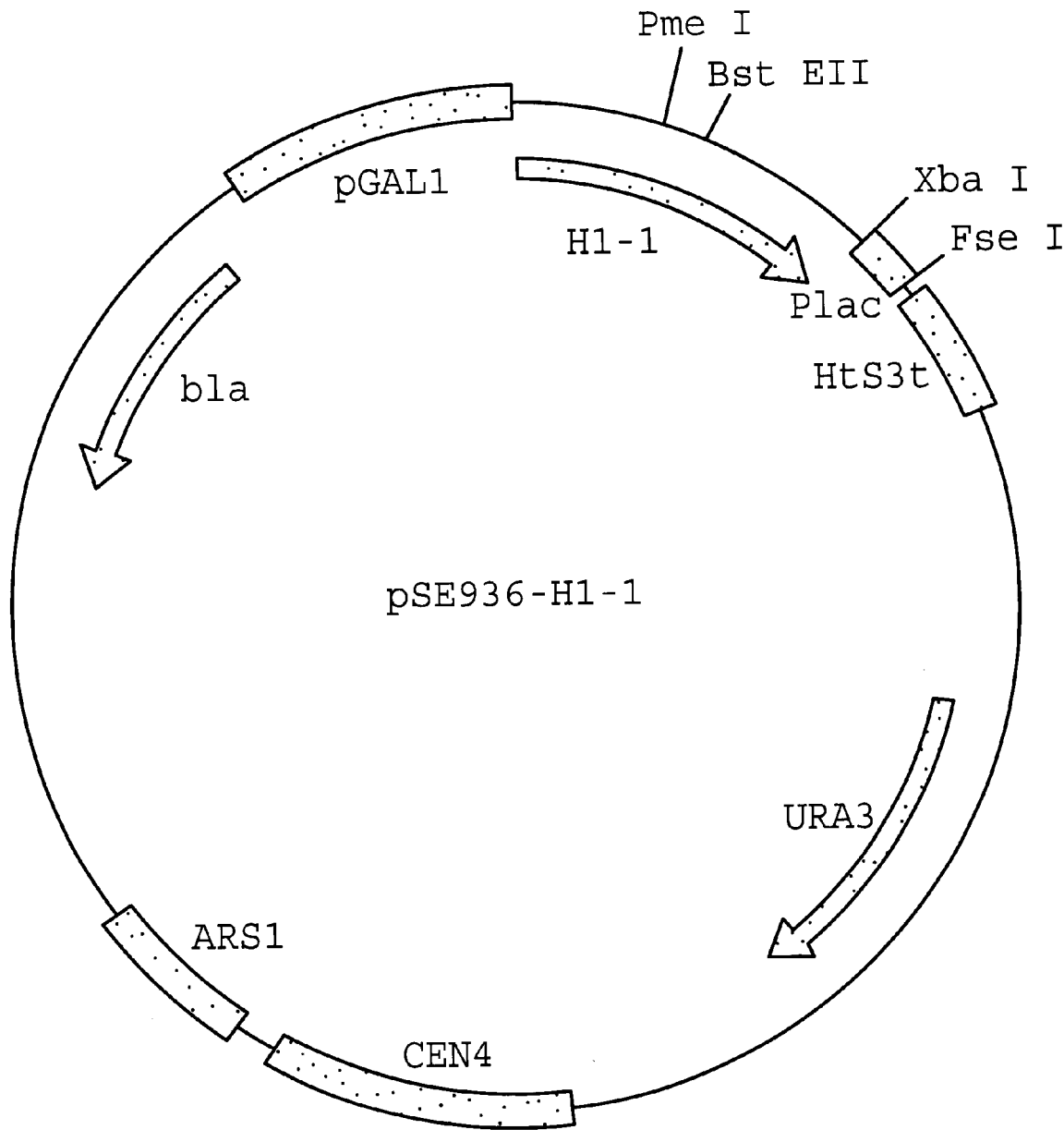
FIG. 13: Plasmid pSE936-H1-1, carrying the cDNA of the H1-1 gene, used as a negative marker in place of RTA.
Figure 14:
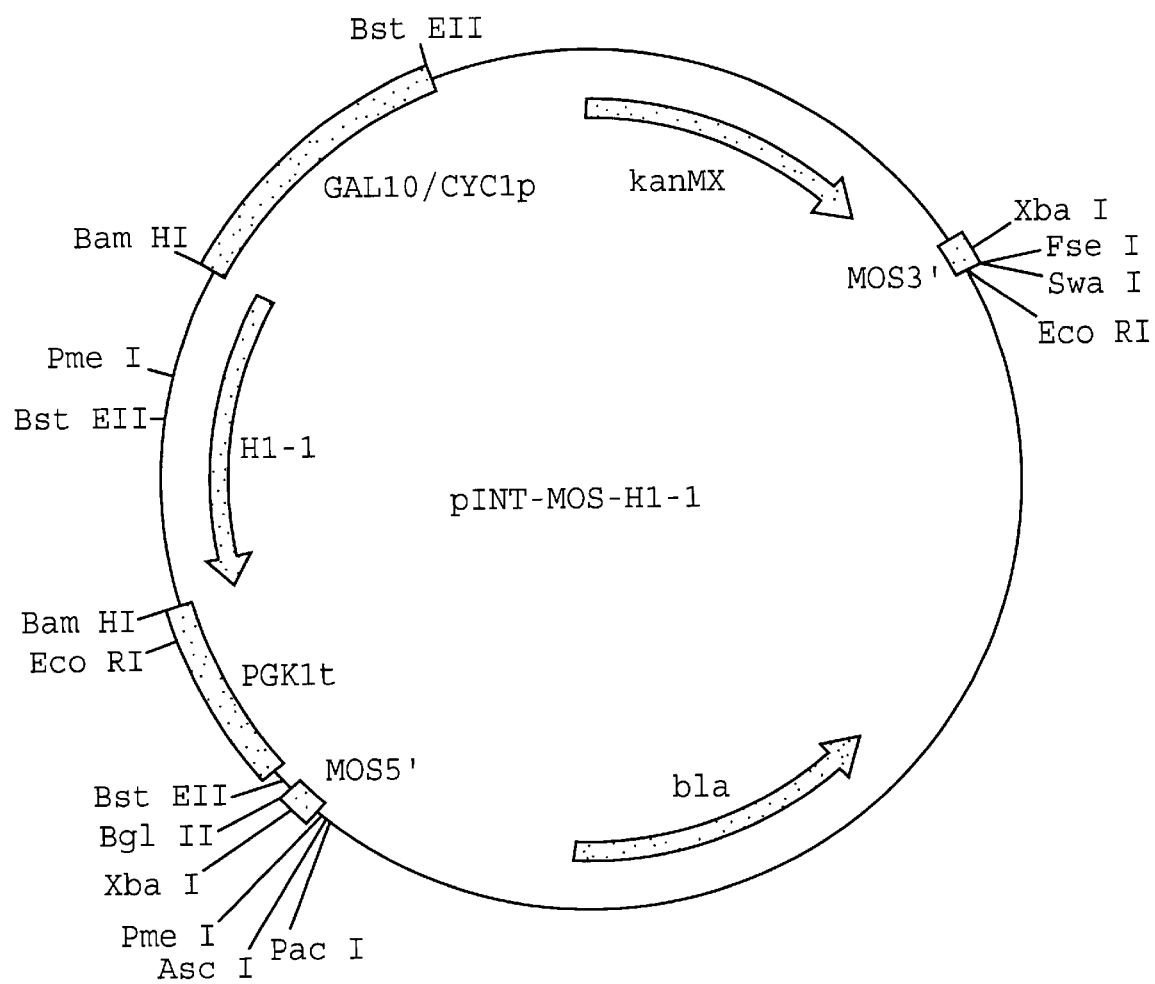
FIG. 14: Plasmid pINT-MOS-H1-1, carrying the excision module whose coding region of RTA gene 5s replaced by the cDNA of H1-1 gene.

Another interesting candidate for playing the role of a negative marker is the H1-1 gene from *Arabidopsis thaliana*. This gene encodes for an histone, i.e. a constituent protein of chromatin of the higher eukaryote organisms. This histone does not seem to inhibit yeast cell growth thanks to a intrinsic toxicity, but thanks to its over-expression which disorganises the nucleus. In order to limit prevention, it is particularly interesting to use as a negative marker a gene which encodes for a protein with no intrinsic toxicity, like a histone, but whose over-expression is able to disorganise a function of the cell and to consequently inhibit its growth.

cDNA of the H1-1 gene is carried by the plasmid SE936-H1-1 (Martinez-Garcia et al. (1996) Gene isolation in *Arabidopsis thaliana* by conditional over-expression of cDNAs toxic to *Saccharomyces cerevisiae*: Identification of a novel early response zinc-finger gene.MGG, 252:587–596) shown FIG. 13. The plasmid pSE936-H1-1 bears thee replication origin ColE1, the promoter lac and the bla gene which are necessary for the replication, expression and selection in *E. coli*, and also the marker URA3, the replication origin ARS1 stabilised by the centromere CEN4 and the expression cassette composed of the promoter GAL1 and the terminator HIS3 which are necessary for the replication, expression and selection in *Saccharomyces cerevisiae*. (Elledge et al. 1991, λYES: A multifunctional cDNA expression vector for the isolation of genes by complementation of yeast and *E. coli* mutations, Proc Natl. Acad. Sci. USA, vol.88, pp. 1731–1735). The cDNA sequence of H1-1 contained in the pSE936-H1-1 may be deduced from the sequence of the H1-1 gene registered in the Genbank by S. Gantt (S. GANTT and T. R LENVIK (1991) *Arabidopsis thaliana* H1 histones: Analysis of two members of a small gene family. Eur.J.BIOCHEM. 202:1029–1039) available under the numero X62458. The cDNA of the H1-1 gene is amplified by PCR in using primers H1 and H2 introducing a BamHI site at the ends 5' and 3' of the PCR product. The PCR product corresponding to H1-1 is digested by BamHI and cloned into the BamHI site of the plasmid pINT-MOS at the place of RTA, giving the plasmid pINT-MOS-H1-1 (FIG. 14).

5) Introduction of an expression gene into the integrative plasmid pINT-MOS

This last step will of course only be carried out in the case where a gene of interest has to be introduced into the genome. To do this, the gene is inserted at the level of the PmeI or AscI of FseI restriction site present in the plasmid pINT-MOS and/or at the level of the AscI or FseI restriction site present in the plasmid pINT-MOS-H1-1, in which the PmeI restriction site cannot be used anymore because of it is also present in the H1-1 marker.

Example 3

Construction of an Excision Module with DRS Sequences MEL

In this example, the two direct repeat sequences allowing the excision of the module by homologous recombination are the fragments derived from the MEL1 gene.

The MEL1 gene is the *Saccharomyces cerevisiae* variant carlsbergensis gene encoding for an alpha-galactosidase which degrades melibiose. MEL1 is absent from bakers' yeasts, which avoids any possible recombination between the DRS sequences MEL and sequences of the genome of the strains of bakers' yeasts. The DRS sequences MEL consist of a sequence of less than or equal to 300 bp chosen from the coding part of the MEL1 gene and preferably containing stop codons positioned in the 6 reading frames for translation. Thus, any translation of the chosen MEL1 sequence to a chimeric polypeptide is avoided.

The said excision module with DRS sequences MEL may be constructed by any strategy which makes it possible to meet the requirements set out above.

According to a particular embodiment, the said excision module is constructed in the following manner:

1) the plasmid pFA6-kanMX4 carrying the dominant selectable marker kanMX serves as base for the construction of the excision module;
2) the DRS sequences MEL are added successively to the plasmid pFA6-kanMX4;
3) the RTA suicide module is inserted.

Each of these steps is carried out in the following manner:

1) the plasmid pFA6-kanMX4 serving as base for the construction is the same plasmid as that used in Example 2 and represented in FIG. 2.
2) The DRS sequences MEL are inserted on either side of the kanMX marker into the plasmid pFA6-kanMX4, in the following manner:

The direct repeat sequence MEL chosen is a DNA fragment of 209 bp situated in the coding region of the MEL1 gene, such as for example the fragment represented by the sequence SEQ ID No. 2.

Figure 9:
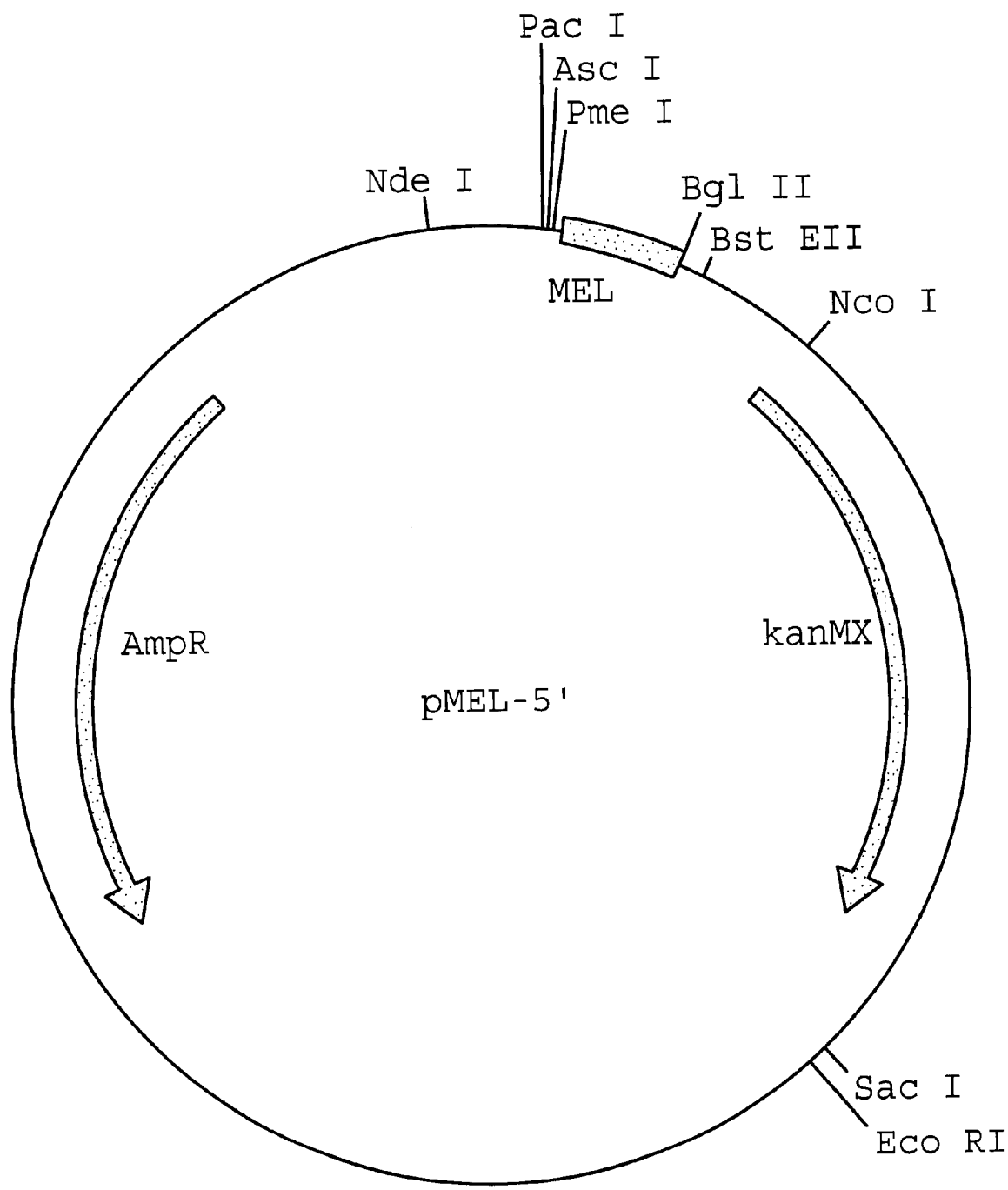
FIG. 9: Plasmid pMEL-5', resulting from the addition of a first direct repeat sequence MEL to the plasmid pFA6-kanMX4 in 3' of the kanMX marker.

The first copy of the DRS sequence MEL is introduced in 5' of the kanMX marker, giving the plasmid pMEL-5' (FIG. 9). For that, the DRS sequence MEL is amplified by PCR using the *Saccharomyces carlsbergensis* genomic DNA as template, with the aid of two primers, L11 and L12. The primer L11 carries the AscI and PmeI restriction sites, the primer L12 carries the BglII restriction site. Thus, during the PCR, the AscI and PmeI restriction sites are introduced in 5' of the DRS sequence MEL and the BglII restriction site is introduced in 3' of the DRS sequence MEL. The product of the PCR is purified and digested with the AscI and BglII enzymes. The plasmid pFA6-kanMX4 was also digested with these enzymes. The two fragments thus obtained are linked giving the plasmid pMEL-5' (FIG. 9).

Figure 10:
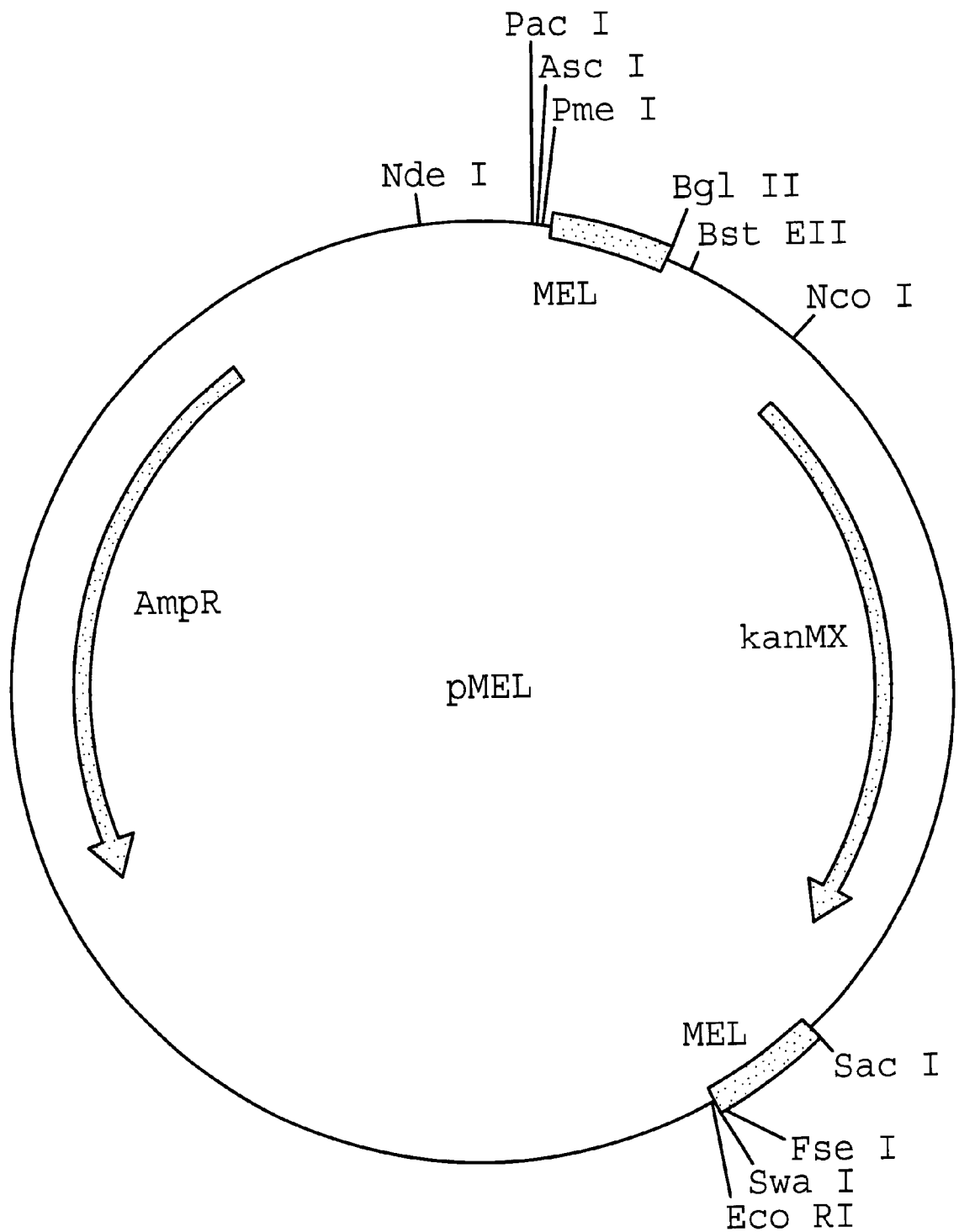
FIG. 10: Plasmid pMEL, resulting from the addition of a second direct repeat sequence MEL to the plasmid pMEL-5'.

Next, the second copy of the DRS sequence MEL is added to the plasmid pMEL-5', in 3' of the kanMX marker. For that, the DRS sequence MEL is amplified by PCR using the *Saccharomyces carlsbergensis* genomic DNA as template in the presence of two primers, L13 and L14. The primer L13 carries the SacI restriction site, the primer L14 carries the FseI, SwaI and EcoRI restriction sites. Thus, during the PCR, the SacI restriction site is introduced in 5' of the DRS sequence and the FseI, SwaI and EcoRI restriction sites are introduced in 3' of the DRS sequence MEL, the EcoRI site being situated at the 3' end of the DRS sequence. The PCR product was purified and digested with the SacI and EcoRI enzymes and introduced into the plasmid pMEL-5', previously digested with the same enzymes. The plasmid pMEL is then obtained (FIG. 10).

Figure 11:
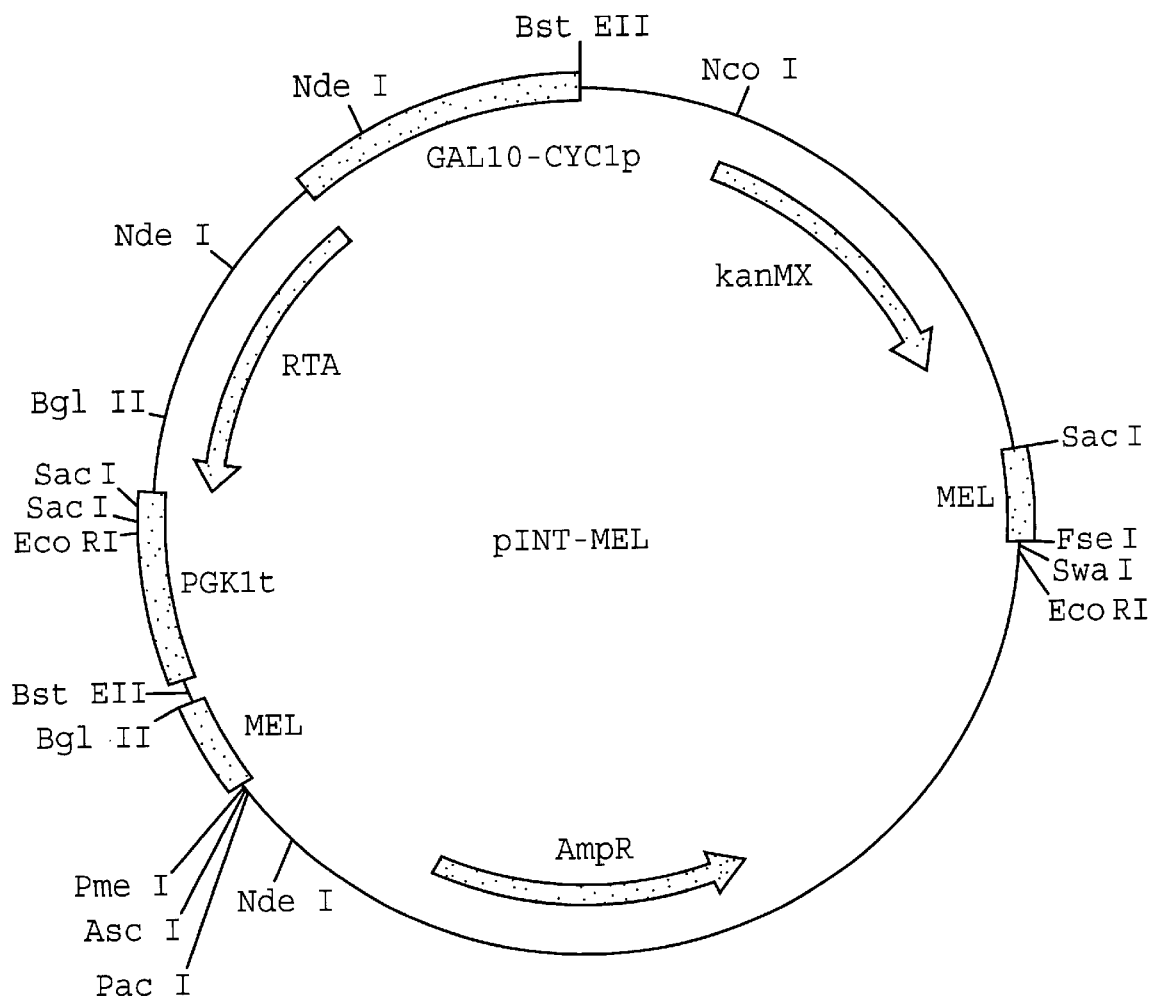
FIG. 11: Plasmid pINT-MEL, carrying the selectable marker kanMX, two direct repeat sequences MEL, and the RTA suicide module.

3) The introduction of the RTA gene is carried out in the same manner as in Example 2 point 3) above. The plasmid obtained is called pINT-MEL (FIG. 11).

Example 4

Deletion of the Different Alleles of the SUC Gene in *Saccharomyces cerevisiae*

*Saccharomyces cerevisiae* possesses several genes dispersed in the genome encoding for enzymes having the same invertase activity, called SUC1, SUC2, and the like. In the bakers' yeast strains, this inverted activity is sometimes a nuisance and it is useful to regulate it. To reduce the level of invertase produced, a number of SUC genes responsible for its production must be inactivated with the aid of different integration/excision cassettes. For that, the excision module according to the invention is assembled between the recombinogenic sequences (RS sequences) capable to integrate into the genomic SUC loci targeted by the recombination with homologous sequences at those loci. Different integration/excision cassettes called CAS-SUC-N, with N=A, B, C, . . . , (these letters specifying the order for using integration cassettes) are constructed and then used successively until the required invertase activity is obtained.

A) Principle of Constructing Integration/Disruption Cassettes CAS-SUC

A CAS-SUC cassette is composed of an excision module and two recombinogenic sequences RS chosen from a region present in all the SUC loci so that the double homologous recombination leading to the integration of the cassette can take place in any SUC locus of the genome.

For example, to carry out 3 disruptions, 3 cassettes are constructed from a plasmid carrying the excision module described in Example 2 above, that is to say the excision module carried by the plasmid pINT-MOS. For the 3 cassettes, the first RS sequence situated at one of the ends of the integration cassette is the same and is called SUC-5'. This fragment of about 200 bp is homologous to the 5' region of the coding sequence of the SUC2 gene. The second RS sequence situated at the opposite end of the integration cassette changes for each of the desired 3 integration events and differentiates the three cassettes. These are three fragments of about 200 bp chosen from the 3' region of the coding sequence of the SUC2 gene, starting from the 3' end of this sequence and going up towards the 5' region. In other words, for the first integration, the outermost fragment called SUC-3'-A is used as recombinogenic sequence together with the SUC-5' fragment; the next integration is carried out with the aid of the middle fragment SUC-3'-B and of the fragment SUC-5', and the last integration is carried out with the innermost fragment SUC-3'-C and the fragment SUC-5'. The different recombinogenic sequences RS chosen should not be homologous with each other. The RS sequences described above may be easily determined from the sequence of the SUC2 gene, identified by the reference YI9402.12 in the MIPS databank. The three cassettes thus obtained are called CAS-SUC-A, CAS-SUC-B and CAS-SUC-C.

The 3 variants of the CAS-SUC cassette are derived from the plasmid pINT-MOS into which the recombinogenic fragments are inserted on either side of the excision module. To do this, the fragments SUC-5', SUC-3'-A, SUC-3'-B, SUC-3'-C are amplified by PCR using the genomic DNA of the laboratory strain CEN.PK122 (EUROSCARF Strain Collection, Germany) . During the PCR, a PacI restriction site is introduced in 5' of the SUC-5' fragment and two STOP codons as well as the AscI restriction site are introduced in 3' of the SUC-5' fragment. Likewise, the 3 fragments SUC-3'-A, SUC-3'-B and SUC-3'-C amplified by PCR are flanked in 5' by the FseI restriction site and in 3' by the SwaI restriction site. These various restriction sites will allow the insertion of the RS sequences into the plasmid pINT-MOS at the level of the corresponding sites. The STOP codons introduced into the reading frame of the SUC2 gene prevent a possible translation of the sequence created by the juxtaposition of a segment of the SUC2 gene and of the first segment forming the mosaic sequence. The risk of synthesizing a chimeric protein is thus avoided.

Figure 12:
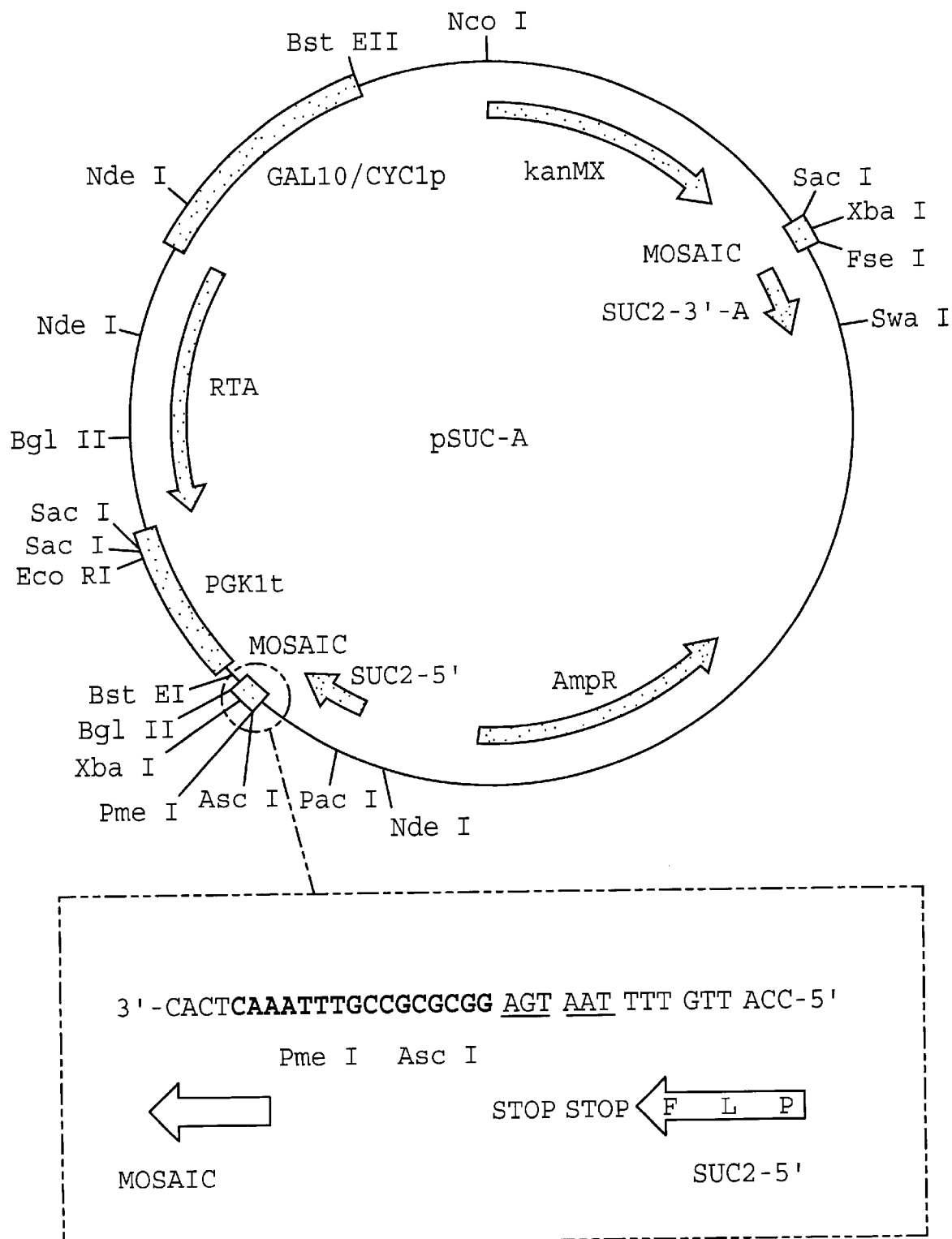
FIG. 12: Plasmid pSUC-A, carrying the cassette for disruption CAS-SUC-A of an allele of the SUC gene in Saccharomyces cerevisiae (SEQ ID NO: 5).

The recombinogenic sequence SUC-5' obtained by PCR is introduced into the plasmid pINT-MOS in 5' of the excision module at the level of the PacI and AscI restriction sites in order to give the plasmid pSUC-5'. Next, the three fragments SUC-3'-A, SUC-3'-B and SUC-3'-C are alternately introduced into this plasmid pSUC-5' in 3' of the excision module, at the level of the FseI and SwaI restriction sites. The three plasmids obtained pSUC-A (FIG. 12), pSUC-B and pSUC-C carry respectively the three integration/excision cassettes CAS-SUC-A, CAS-SU--B and CAS-SUC-C.

B) Deletion of Three Alleles of the SUC Gene by Multiple Integrations/Excisions

The three cassettes CAS-SUC-A, CAS-SUC-B and CAS-SUC-C were used successively.

1) Integration of the CAS-SUC-A Cassette into the *Saccharomyces cerevisiae* Genome The first integration/excision cassette CAS-SUC--A is integrated into a SUC locus of the *Saccharomyces cerevisiae* genome by double homologous recombination. For that, it is extracted from the plasmid pSUC-A by means of a digestion with the PacI and SwaI enzymes, and purified. A strain of *Saccharomyces cerevisiae* is transformed by introducing the integration/excision cassette in linear DNA form into the cells.

To select the cells where the disruption of a first allele of the SUC gene has taken place, that is to say the cells having integrated at the SUC locus the cassette comprising the selectable marker kanMX and the RTA suicide module, the transformants are plated on YPD medium (1% yeast, 2% bactopeptone, 2% glucose extract) containing geneticin in an amount of 200 $\mu$g per ml of medium. Each clone which has integrated the cassette is resistant to geneticin and forms a colony. The specific integration of the CAS-SUC-A cassette at the level of an SUC locus leading to the deletion of a first SUC allele is checked by Southern hybridization (Sambrook et al., Molecular Cloning, a Laboratory Manual, Cold Spring Harbor Laboratory Press, 1989, vol. 2, pp. 9.31–94.6).

2) Excision of the Heterologous Sequences

At the level of the deleted SUC locus, all the sequences heterologous to the *Saccharomyces cerevisiae* genome must be eliminated. The excision of the integration/excision module results from a recombination at the level of the 2 DRS sequences and from the excision of the DNA loop thus formed, the strains having carried out this excision being selected by means of the induction of i:he expression of the RTA gene. To induce the expression of the RTA gene, the transformants are precultured on a liquid medium containing galactose as sole source of carbon and then plated on a standard "galactose" agar medium. This medium makes it possible to select the transformant clones not producing the toxin encoded by the RTA gene. To check the elimination of the kanMX marker, the said selected transformant clones are replicated on YPD medium containing geneticin (200 $\mu$g/ml) in order to verify the loss of the resistance to geneticin. This double selection makes it possible to isolate transformant clones carrying a deletion in a first SUC locus, having excised the selectable markers RTA and kanMX.

After excision of the integration/excision module, only one DRS sequence remains in place, flanked by the RS sequences SUC-5' and SUC-3'-A respectively in 5' and in 3'. Finally, the deletion of the SUC allele and the loss of the selectable markers are verified by sequencing.

3) Integration and Excision of the Cassettes CAS-SUC-B and CAS-SUC-C

The second and third integration/disruption cassettes CAS-SUC-B and CAS-SUC-C are used successively to delete a second copy and then a third genomic copy of the SUC locus, in the *Saccharomyces cerevisiae* strain previously constructed of which a first copy of a SUC locus has been disrupted. The cassettes CAS-SUC-B and CAS-SUC-C successively used will be able to integrate at the level of the SUC loci, preferably at the level of nontransformed alleles, taking into account the change of RS in 3' of the integration site.

The cassettes CAS-SUC-B and CAS-SUC-C are extracted from the plasmids PSUC-B and pSUC-C by means of digestion with the PacI and SwaI enzymes, and then purified. The integration/excision protocol described above for CAS-SUC-A is repeated successively for CAS-SUC-B and then CAS-SUC-C under identical conditions, namely transformation and selection of the transformants which have integrated the cassette, selection of the transformants which have excised the selectable markers. Finally, the effect of the deletions at the SUC loci is controlled by assaying the residual invertase activity and the elimination of the selectable markers is verified by sequencing and by hybridization (Southern hybridization).

Example 5

Deletion of the URA3 Genes in the Diploid Strain Y55.LD1.

Another application of the cassette is the construction of an uracil auxotrophic mutant of the baker's yeast strain Y55.LD1 (diploid laboratory strain, prototroph, isogenic with the strain Y55 described by McCusker, J. H and J. E. Haber (1988) Cycloheximide-resistant temperature sensitive lethal mutations of *Saccharomyces cerevisae*. Genetics 119: 303–315). Compared to the original strain Y55, strain Y55.LD1 carries the homozygous deletion of the HO gene, this deletion is described by Hunter, N. Chambers, S. R., Louis, E. et R. H. Borts (1996). The mismatch repair system contributes to meiotic sterility in an interspecific yeast hybrid. EMBO J.15: 1726–1733. For transformation of this strain with yeast vectors carrying the URA3 gene as a marker, it is necessary to make this strain auxotrophic for uracil. Therefore the 2 copies of the URA3 gene present in this strain are deleted by using the integration/excision cassette according to the invention.

The excision module according to the invention is placed between two recombinogenic sequences able to integrate into the genomic *Saccharomyces cerevisiae* URA3 loci by recombination with the homologous sequences present at those loci. The two copies of the URA3 gene present in the strain Y55.LD1 are successively deleted with the same integration/excision cassette, which is named CAS-URA.

A/Principle of Constructing the Integration/Excision Cassette.

In analogy to what has been described above for the integration/excision cassette CAS-SUC, the CAS-URA cassette is composed of the excision module and the two recombinogenic sequences RS that have been chosen in the coding region of the gene, so that the double recombination leads to the replacement of the coding region of the URA3 gene by the excision module. The first RS sequence which is located at one end of the integration cassette is named URA3-5' and is a fragment of about 600 bp homologous to the promoter region of the URA3 gene. The second SR sequence which is located at the other end of the integration cassette is named URA3-3' and is a fragment of about 600bp and is homologous to the terminator region at the 3' end of the coding region of the URA3 gene.

The CAS-URA cassette is derived from the plasmid pINT-MOS in which the recombinogenic fragments are inserted to either part of the excision module. To do this, the fragments URA-5' and URA-3' are amplified by PCR in using genomic DNA of the laboratory strain Y55.LD1. During the PCR, a PacI restriction site is introduced at the 5' end of the URA3-5' fragment and the AscI restriction site is introduced at 3' end of the URA3-5' fragment. Likewise, the URA3-3' fragment amplified by PCR is flanked at the 5' end by a FseI restriction site and at the 3' end by a SwaI restriction site.

Figure 15:
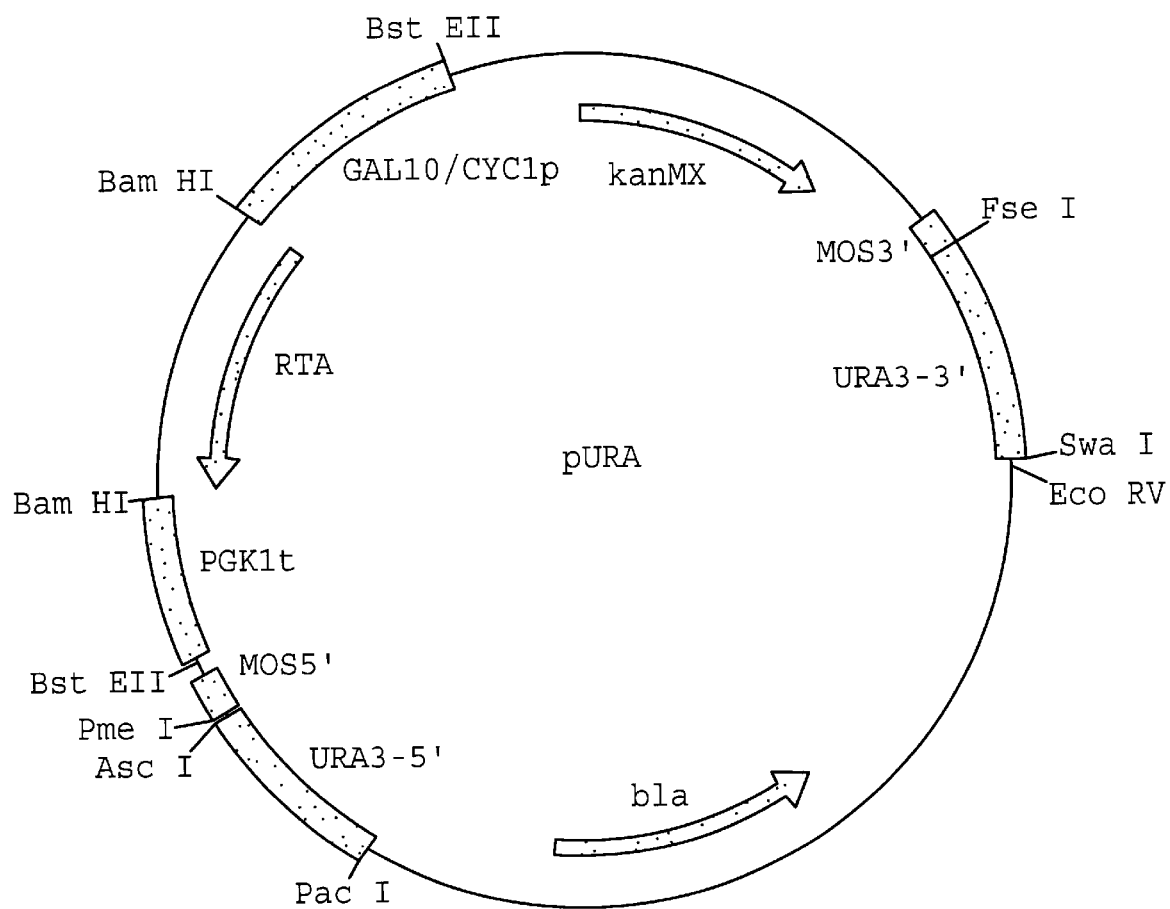
FIG. 15: Plasmid pURA, carrying the CAS-URA deletion cassette of the URA3 gene.

The recombinogenic sequence URA3-5' obtained by PCR is introduced into the plasmid pINT-MOS at 5' of the excision module at the level of the PacI and AscI restriction sites resulting in plasmid pURA-51. The URA3-3' fragment is introduced into the plasmid pURA-5' at 3' of the excision module, at the level of the FseI and SwaI restriction sites. The obtained plasmid is named pURA. (FIG. 15)

B/Deletion of the Two Alleles of the URA3 Gene by Multiple Integration/Excisions.

The strain Y55.LD1 is transformed by introducing the integration/excision cassette CAS-URA in linear DNA form. This cassette is extracted from the plasmid pURA via digestion by PacI and SwaI restriction enzymes and subsequently purified.

The integration of the cassette into the genomic URA3 locus, and then the excision of the integration/excision module are controlled by the presence or the absence of the 2 dominant markers, using the same protocols as described above for the example 4.

Integration and excision of the CAS-URA cassette at the level of the second URA3 locus are performed the same way.

The effect of the deletions of the URA3 loci is controlled on agar plates containing a 2% glucose minimal medium by verification of the absence of cell growth. The elimination of the selectable markers is verified by sequencing and Southern hybridisation on haploid cells from several tetrads obtained after sporulation of the modified diploid strain. The obtained auxotrophic strain is named Y55.LD2.

Example 6

Construction and Implementation of Integration/Excision Cassettes for Multiple Insertion of a Gene of Interest Coding for a Protein Which is Not Naturally Produced by *Saccharomyces cerevisiae*.

The procedure is carried out as in the example 4 or 5 except that at the PmeI restriction site of the plasmids pSUC-A, pSUC-B, pSUC-C or pURA, a DNA fragment consisting of the coding part of the gene of interest, or its cDNA, is introduced into the cassette, under the *Saccharomyces cerevisiae* promoter and terminator, the said fragment to be introduced into the integration/excision cassette being flanked at each end by a PmeI site.

It is possible, for example, to introduce successively three copies of the cDNA encoding for an enzyme such as *Trichoderma reesei* xylanase Xyl2 or Xln2 into three *Saccharomyces cerevisiae* SUC loci, and to verify, on the one hand, the production of xylanase by the transformed strains and the absence of any exogenous DNA with the exception of that corresponding to the coding part of the Trichoderma Xyl2 or Xln2 gene. It is also possible to choose URA3 loci for the integration, knowing that at least one active URA3 locus must be kept so that the strain will not become auxotrophic for uracil.

Example 7

Construction of a Yeast Expression Vector Containing No Useless Heterologous or Exogenous Sequences.

The module composed of the two mosaic sequences and the negative dominant marker is used to construct a high copy E. coli-yeast shuttle plasmid.

Once introduced in the yeast, a homologous recombination between the two mosaic sequences leads to a loss of all sequences derived from E. coli as well as the negative marker.

The remaining plasmid consists only of yeast sequences and of the gene of interest. It can be used for high-copy gene expression without any foreign DNA in the yeast other than—in case of a heterologous gene—the gene of interest.

The plasmid pINT-MOS (FIG. 8) is the platform for the construction of this shuttle plasmid. An oligonucleotide linker comprising the unique sites EcoRI, AscI, PmeI, SwaI, PacI and HindIII is introduced between the two mosaic DRS of this plasmid. (A unique site is a site which is present just once in the construction).

EcoRI and HindIII are used for integration of the yeast 2 micron origin of replication and URA3 sequences, respectively. The restriction sites AscI, PmeI, SwaI and PacI provide potential sites for integration of an expression cassette. Therefore all of those sites that were already present in the plasmid pINT-MOS need to be removed. For elimination of the EcoRI, SwaI and EcoRV sites, the plasmid pINT-MOS is digested with SwaI and EcoRV restriction enzymes and re-ligated. Several n.ore restriction sites are replaced by a BstEII site via digestion of resulting plasmid with PmeI and PvuII endonucleases, removing with this step the fragment comprising those two sites and all sites located between them (HindIII, AscI, SalI and PacI). The linear fragment is ligated to a short linker oliginucleotide consisting of the 7 bp of the BstEII endonuclease recognition sequence (GGTCACC).

Figure 16:
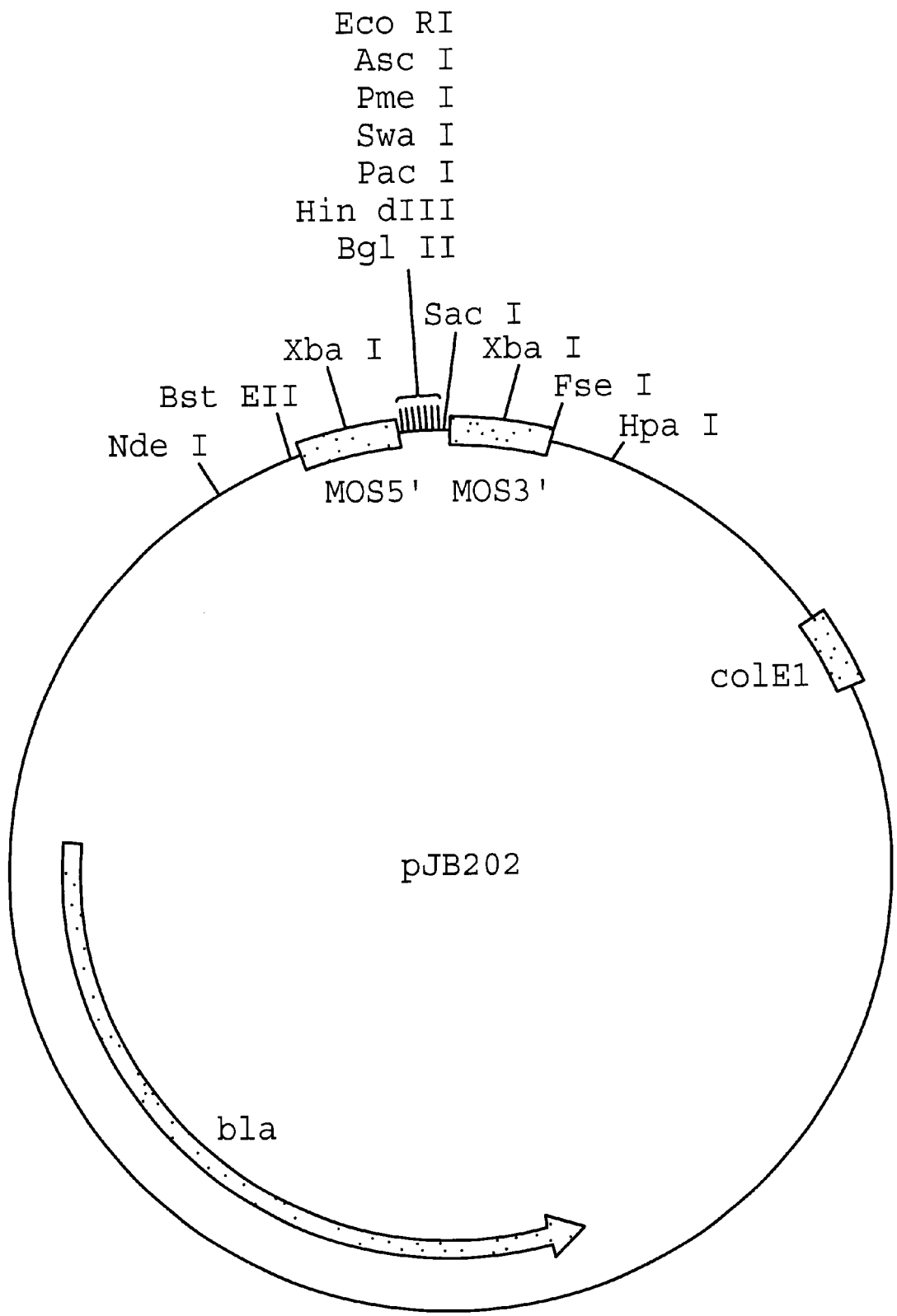
FIG. 16: Plasmid pJB202, resulting from the substitution of the negative and positive selectable markers of pINT-MOS by a linker oligonucleotide containing the unique restriction sites EcoRI, AscI, PmeI, SwaI, PacI and HindIII.

Subsequently, the negative and positive selection markers are replaced by a linker. This linker is composed of two oligonucleotides (SEQ ID Nos: 3 and 4) that have been hybridised beforehand, thus giving the above mentioned restriction sites. To do so, the plasmid is digested with the endonuclease BglII and SacI, the fragment containing the two markers is removed and the remaining vector is ligated with the above mentioned linker. The resulting plasmid is named pJB202 (FIG. 16). As above mentioned, the linker obtained via hybridisation of the 2 sequences SEQ ID Nos 3 and 4, introduces into this plasmid the EcoRI, AscI, PmeI, PacI and HindIII and the reconstituted SacI and BglII restriction sites.

Figure 17:
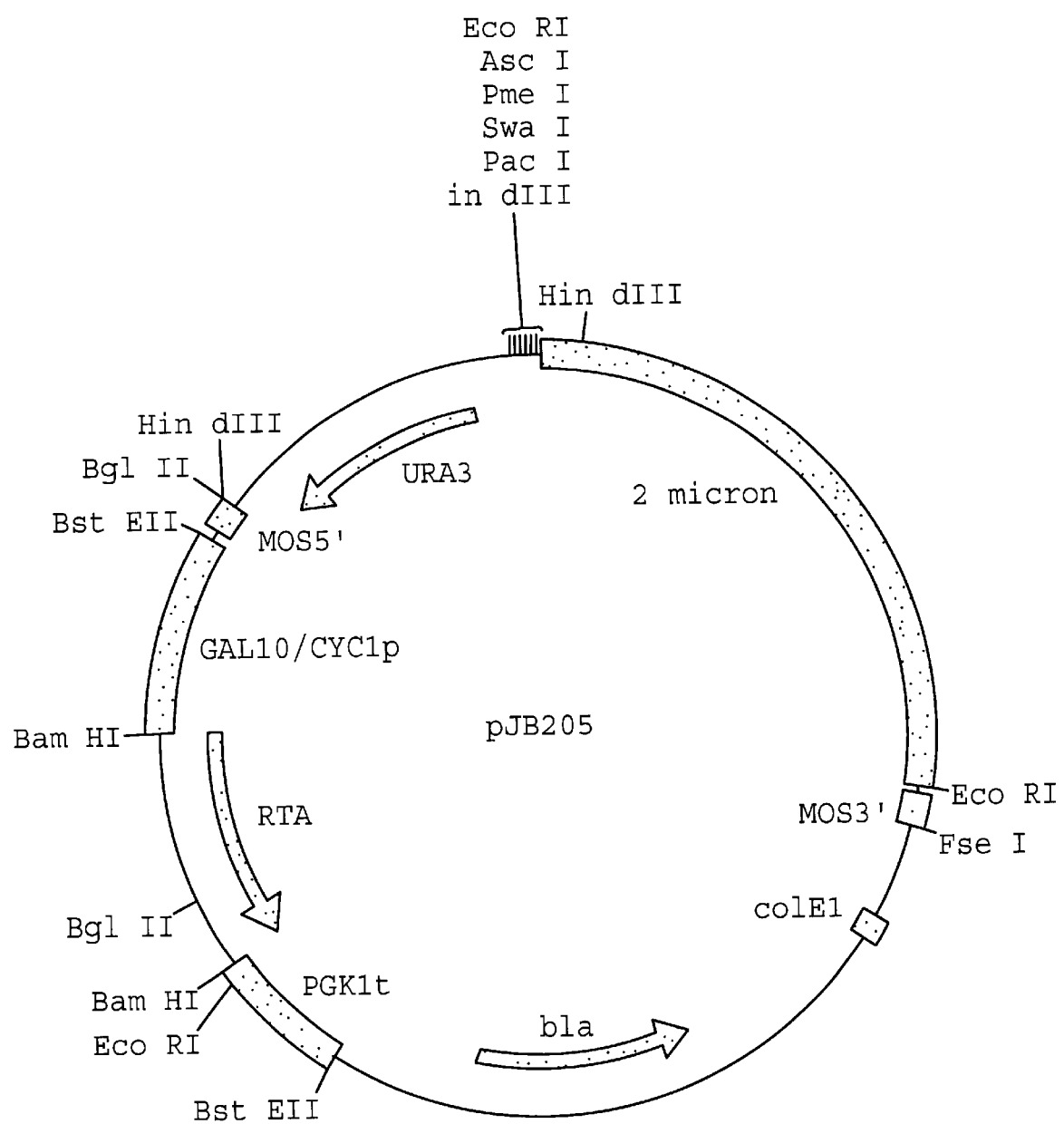
FIG. 17: Plasmid pJB205 resulting from the successive addition of the URA3 gene, of the 2 micron fragment and of the RTA module to the plasmid pJB202.

The URA3 gene is isolated from plasmid YEp24 (D. Botstein, Falco, S. C., Stewart, S., Brennan, M., Scherer, S., Stinchcomb, D. T., Struhl, K. and R. Davis (1979) Sterile host yeasts (SHY): a eukaryotic system of biological containment for recombinant DNA experiments. Gene 8: 17–24) after digestion of YEp24 with HindIII. The resulting 1.2 kb fragment is inserted into HindIII site of plasmid pJB202, yielding plasmid pJB203. The yeast 2 micron fragment is also isolated from plasmid YEp24. Therefore, plasmid YEp24 is digested with EcoRI and the 2.2 kpb fragment containing the 2 micron origin of replication is isolated. This fragment is ligated into plasmid pJB203, previously digested with EcoRI. The resulting plasmid pJB204, is digested with the endonuclease BstEII and ligated to the PCR product described in example 2, containing the RTA module. The resulting plasmid is named pJB205 and is shown in FIG. 17. It contains the fragment comprising the E. coli origin of replication and the βlactamase (bla) or (Amp$^r$) coding region from plasmid pSP72 (Promega SA, USA) linked to the RTA module, both separated by two direct mosaic DRS sequences from the module only containing yeast DNA.

The resulting plasmid PJB205 may be used to transform yeast strains which are auxotrophic for uracil. A similar vector may be constructed in order to permit the transformation of prototrophic yeast strains. In this case, the URA3 gene must be replaced by a dominant positive marker of yeast origin, i.e. homologous for the yeast. Such markers are quoted in the description above. Such a plasmid is named hereinafter pJB208.

Example 8

Production of the Lactate Dehydrogenase Enzyme by Saccharomyces cerevisiae Thanks to a High Number of High Copy Plasmids.

The ldhL gene, coding for lactate dehydrogenase, from Lactobacillus plantarum is introduced with its yeast expression elements into the plasmid pJB205 described in example 7.

The expression cassette of the ldhL gene from L. plantarum under control of the Saccharomyces cerevisiae ADH1 promoter and terminator is obtained from the plasmid pVT.LDHp.

This plasmid pVT.LDHp is constructed by introducing into the plasmid pVT100-U (T. Vernet, D. Dignard and D. Y. Thomas (1987) A family of yeast expression vectors containing the phage f1 intergenic region. Gene 52: 225–233), at the level of its XbaI site, a PCR product containing the coding region of the ldhL gene from Lactobacillus plantarum, amplified by PCR from plasmid pGIT005 (T. Ferain, D. Garmyn, N. Bernard, P. Hols and J. Delcour (1994) Lactobacillus plantarum ldhL Gene: Overexpression and Deletion. J. Bacteriol. 176: 596–601) and a XbaI site at either end.

The expression cassette of the ldhL gene is amplified by PCR from the plasmid pVT.LDHp in using two primers introducing at each end of the PCR product the PmeI site.

Figure 18:
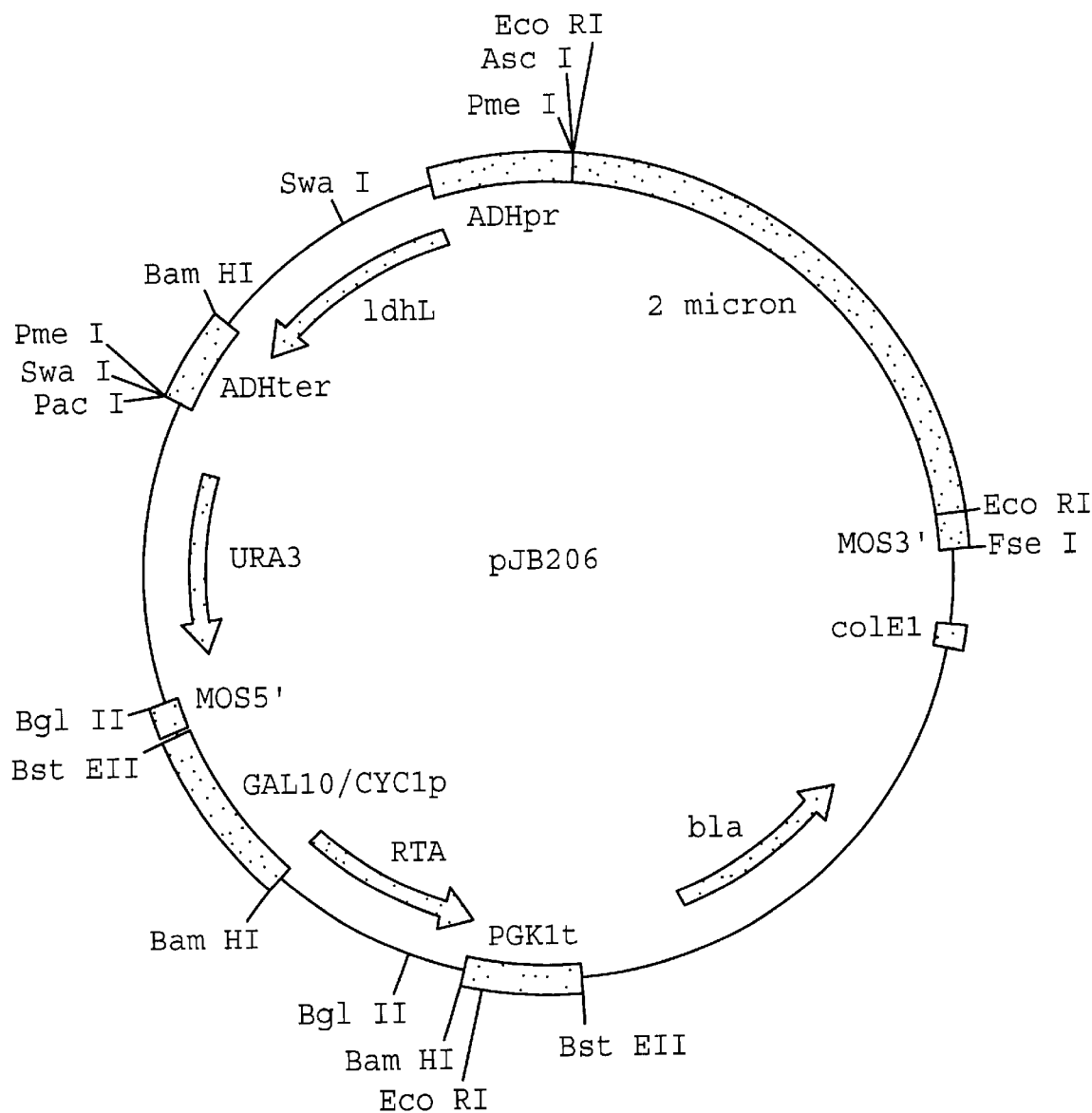
FIG. 18: Plasmid pJB206 resulting from the addition of the expression cassette of the ldhL gene to the plasmid pJB205.

The resulting PCR product is purified, digested with the endonuclease PmeI and ligated into the plasmid pJB205, previously linearized by PmeI digestion, resulting in the plasmid pJB206 (FIG. 18).

Figure 19:
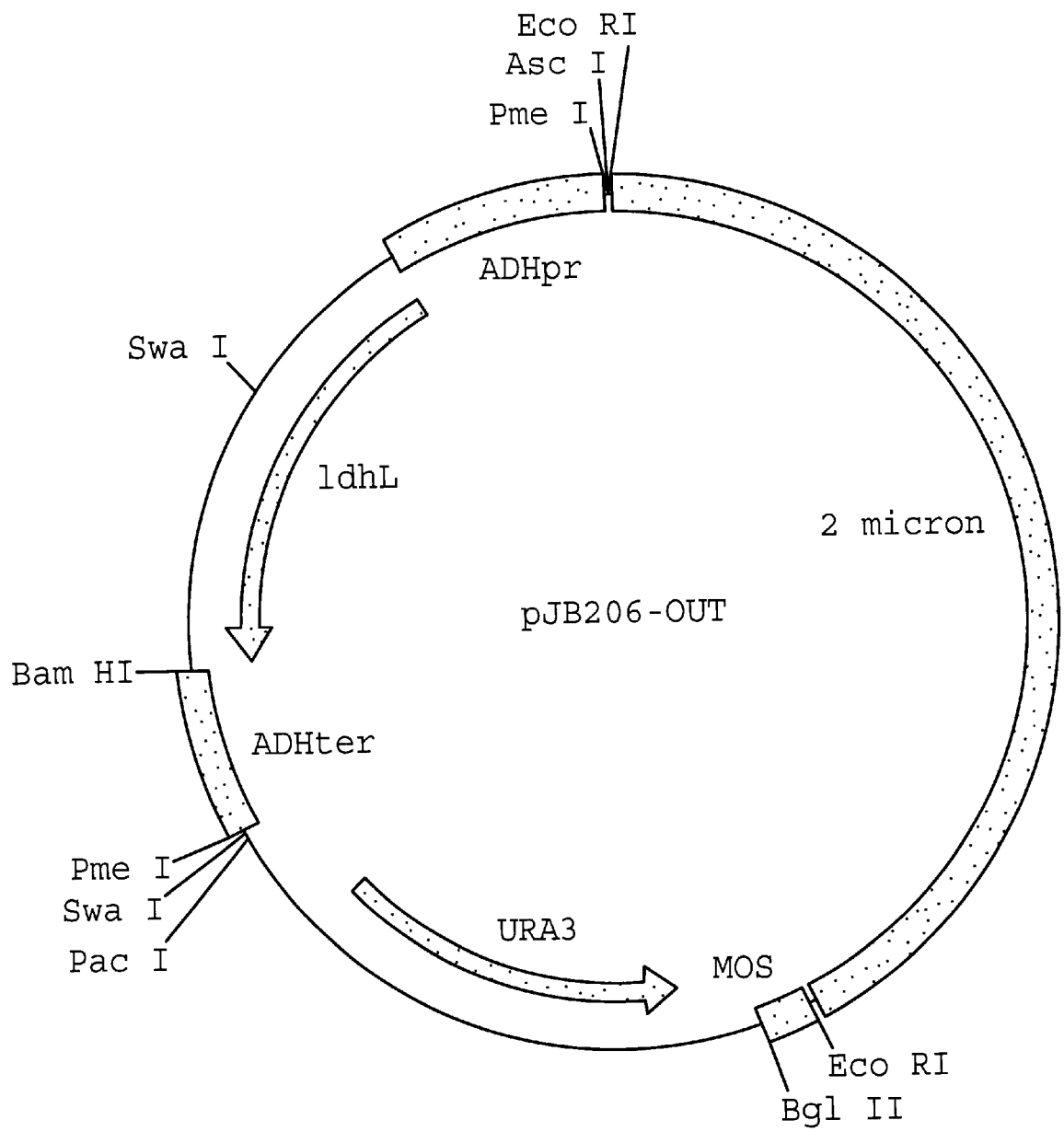
FIG. 19: Plasmid pJB206-OUT resulting from the excision of the fragment containing the negative marker and the E. coli DNA fragment out of the plasmid pJB206.

The baker's yeast strain Y55.LD2 (2n Δura3 ::MOS) constructed in example 5, is transformed with the resulting plasmid pJB206. Transformants are selected on minimal medium containing 2% galactose as sole carbon source. The galactose present in the medium induces expression of the negative dominant marker gene. It therefore allows to select the cells carrying one or several plasmids having lost the DNA fragment containing this negative marker and the DNA of E. coli origin via homologous recombination between the two mosaic fragments. This medium leads to selection of transformants containing the plasmid pJB206-OUT (FIG. 19). For verification of the loss of the negative marker and the E. coli DNA fragment, via excision, the plasmid(s) is (are) isolated from one transformant and analysed by PCR and sequencing.

To test the lactic acid production capacity of this clone, the transformant is grown for 48 hours on a minimal medium containing 5% glucose as carbon source to a final OD$_{600}$ of 4. Cells are removed from the culture medium by centrifugation and presence of lactic acid is determined with the lactate kit supplied by Roche Diagnostics (Germany). Compared with the control strain, the transformant produces under these conditions significant amounts of lactic acid.

In a modified version of this example, the expression of a gene encoding for lactate dehydrogenase can be performed in using a prototrophic yeast strain like the yeast strain Y55.LD1, transformed with a type pJB208 shuttle plasmid, of which the auxotrophic complementation marker as the URA3 gene, is replaced by a positive dominant yeast marker homologous with the yeast genome. In this case, the excision of all *E. coli* sequences, of the inducible negative marker, and of one copy of the two mosaic RS sequences, will similarly result in a type pJB209-OUT plasmid comprising only:

a yeast 2 micron replication origin.

a yeast homologous marker the expression system of the gene of interest.

one mosaic sequence.

---

What is claimed is:

1. A DNA cassette intended for the transformation of a yeast host strain comprising
at least one excision module comprising:
one negative dominant selectable marker;
two direct repeat sequences (DRS), the length of which is at least 30 basepairs (bp), wherein said DRS do not contain exogenous DNA and are non recombinogenic: with the genome of the yeast host strain, wherein the two direct repeat sequences flank a fragment comprising said negative dominant selectable marker and wherein the two DRS comprise (a) mosaic sequences comprising an assembly of fragments of various DNA sequences of a yeast strain belonging to the same genus as said yeast host strain or (b) one or more DNA sequence(s) not present in the yeast host strain, but present in other strains belonging to the same genus of said yeast host strain;
and at least one rare restriction site at each end of said excision module.

2. The DNA cassette of claim 1, comprising at least 3 rare restriction sites at each end of said excision module.

3. The DNA cassette of claim 1, intended for the integration of at least one DNA sequence encoding a protein of interest or for the inactivation of a gene of said yeast host strain, further comprising:
two recombinogenic DNA sequences (RS) corresponding to the desired insertion site in the yeast host strain, flanking said excision module, and
at least one DNA sequence encoding a protein of interest or for the inactivation of a gene of said yeast host strain located between said two RS and outside of said excision module.

4. The DNA cassette of claim 1, further comprising any elements necessary for the expression of a protein of interest.

5. The DNA cassette of claim 1, wherein the dominant negative marker is an inducible marker whose DNA codes for a product toxic for the host cell.

6. The DNA cassette of claim 1, comprising at least five rare restriction sites at each end of said excision module.

7. The DNA cassette of claim 1 or 2, wherein the lengths of the fragments in the mosaic sequences of the DRS are between 10 to 30 bp.

8. The DNA cassette of claim 1 or 2, wherein the lengths of the DNA sequence(s), not present in the host strain, of the DRS are between 10 to 30 bp.

9. The DNA cassette of claim 1 or 2, wherein the DRS comprise one or more fragment(s) of the MEL1 gene, wherein the length of the fragments is between 10 to 30 bp.

10. The DNA cassette of claim 1 or 2, wherein each of the DRS contains from 80 to 300 bp.

11. The DNA cassette of claim 1 or 2, wherein each of the DRS contains at most about 200 bp.

12. The DNA cassette of claim 1 or 2, wherein the negative dominant marker is an RTA suicide gene under the control of an inducible GAL promoter.

13. The DNA cassette of claim 1 or 2, wherein the negative dominant marker is an RTA suicide gene under the control of a promoter chosen in the group consisting of the GAL10 promoter and the GAL10-CYC1 promoter.

14. The DNA cassette of claim 1 or 2, wherein the dominant negative marker is the *Arabidopsis thaliana* H1-1 gene under the control of a conditional or inducible promoter.

15. The DNA cassette of claim 1 or 2, wherein the DRS are noncoding.

16. The DNA cassette of claim 2, intended for the integration of at least one DNA sequence encoding a protein of interest or for the inactivation of a gene of said yeast host strain, further comprising:
two recombinogenic DNA sequences (RS) corresponding to the desired insertion site in the yeast host strain, flanking said excision module, and
at least one DNA sequence encoding a protein of interest or for the inactivation of a gene of said yeast host strain located between said two RS and outside of said excision module.

17. The DNA cassette of claim 2, further comprising any elements necessary for the expression of a protein of interest.

18. The DNA cassette of claim 2, wherein the dominant negative marker is an inducible marker whose DNA codes for a product toxic for the host cell.

19. The DNA cassette of claim 3, wherein said excision module further comprises a dominant positive selectable marker, wherein said positive marker and said negative marker are flanked by the DRS.

20. The DNA cassette of claim 3, further comprising any elements necessary for the expression of said protein of interest.

21. The DNA cassette of claim 3 or 16 that does not contain any exogenous DNA between the DRS and the adjacent recombinogenic sequences.

22. The DNA cassette of claim 16, wherein said excision module further comprises a dominant positive selectable marker, wherein said positive marker and said negative marker flanked by the DRS.

23. The DNA cassette of claim 16, further comprising any elements necessary for the expression of said protein of interest.

24. The DNA cassette of claim 19, comprising two dominant selectable markers, wherein the positive selectable marker is a resistance marker belonging to the group consisting of DNA coding for proteins for resistance to antibiotics and DNA coding for proteins for resistance to molecules toxic to the host.

25. The DNA cassette of claim 22, comprising two dominant selectable markers, wherein the positive selectable marker is a resistance marker belonging to the group consisting of DNA coding for proteins for resistance to antibiotics and DNA coding for proteins for resistance to molecules toxic to the host.

26. A yeast transformed with the cassette of claim 1, said yeast comprising only yeast DNA, wherein the DRS of the cassette are non-coding.

27. A yeast transformed with the cassette of claim 2, said yeast comprising only yeast DNA, wherein the DRS of the cassette are non-coding.

28. The yeast of claim 26 or 27, wherein at least one gene has been inactivated by said cassette.

29. The yeast of claim 26 or 27, wherein all the copies of the same gene have been inactivated.

30. The yeast of claim 26 or 27, wherein the yeast is a Saccharomyces strain.

31. An *Escherichia coli* (*E. coli*)-yeast shuttle plasmid, comprising two separate regions wherein:
said first region comprises said DNA cassette of claim 1 wherein said excision module comprises said negative marker, an *E. coli* replication origin and a selectable marker for *E. coli*, said first region being flanked by the DRS; and wherein
said second region comprises a yeast 2 micron replication origin, a selectable marker of yeast origin, and an expression system with at least one DNA fragment coding for a protein of interest;

wherein said first and second regions are delimited by said two DRS of said DNA cassette.

32. The shuttle plasmid of claim 31 as a high copy expression plasmid, wherein the first region of the *E. coli*-yeast shuttle plasmid comprising the negative dominant marker, the *E. coli* replication origin, and the selectable marker for *E. coli*, has been eliminated by excision.

33. The shuttle plasmid of claim 1, wherein the selectable maker of yeast origin is an auxotrophy complementation marker.

34. An *E. coli*-yeast shuttle plasmid, comprising two separate regions wherein:

said first region comprises said DNA cassette of claim 2 wherein said excision module comprises said negative marker, an *E. coli* replication origin and a selectable marker for *E. coli*, said first region being flanked by the DRS; and wherein:

said second region comprises a yeast 2 micron replication origin, a selectable marker of yeast origin, and an expression system with at least one DNA fragment coding for a protein of interest;

wherein said first and second regions are delimited by said two DRS of said DNA cassette.

35. The shuttle plasmid of claim 34 as a high copy expression plasmid, wherein the first region of the *E. coli*-yeast shuttle plasmid comprising the negative dominant marker, the *E. coli* replication origin, and the selectable marker of *E. coli*, has been eliminated by excision.

36. The shuttle plasmid of claim 34, wherein the selectable maker of yeast origin is an auxotrophy complementation marker.

37. A method of transforming an auxotrophic yeast with the shuttle plasmid of claim 33 or 36, to obtain a high copy expression of at least one DNA sequence encoding a protein of interest, comprising:

transforming the yeast with said shuttle plasmid of claim 33 or claim 36;

selecting, on medium that does not contain the element for which the yeast is auxotrophic, the yeasts which only contain plasmids out of which the first region has been excised.

38. A method of integrating a DNA sequence encoding a protein of interest or of inactivating a gene in yeast, comprising:

transforming said yeast with the excision/integration DNA cassette of claim 3;

selecting the yeasts having integrated said cassette;

and then, after culturing, selecting the yeasts in which the part of the cassette between the DRS has been excised by recombination between the DRS sequences, by selecting the yeasts not containing the negative marker.

39. A method of integrating a DNA sequence encoding a protein of interest or of inactivating a gene in yeast, comprising:

transforming said yeast with the excision/integration DNA cassette of claim 4;

selecting the yeasts having integrated said cassette by means of a positive marker;

and then, after culturing, selecting the yeasts in which the part of the cassette between the DRS has been excised by recombination between the DRS, by selecting the yeasts not containing the negative marker.

40. A method of integrating a DNA sequence encoding a protein of interest or of inactivating a gene in yeast, comprising:

transforming said yeast with the excision/integration DNA cassette of claim 16;

selecting the yeasts having integrated said cassette;

and then, after culturing, selecting the yeasts in which the part of the cassette between the DRS has been excised by recombination between the DRS, by selecting the yeasts not containing the negative marker.

41. A method of integrating a DNA sequence encoding a protein of interest or of inactivating a gene in yeast, comprising:

transforming said yeast with the excision/integration DNA cassette of claim 17;

selecting the yeasts having integrated said cassette by means of a positive marker;

and then, after culturing, selecting the yeasts in which the part of the cassette between the DRS has been excised by recombination between the DRS, by selecting the yeasts not containing the negative marker.

42. A method of integrating a DNA sequence encoding a protein of interest or of inactivating a gene in yeast, comprising:

transforming said yeast with the excision/integration DNA cassette of claim 19;

selecting the yeasts having integrated said cassette by means of said positive marker;

and then, after culturing, selecting the yeasts in which the part of the cassette between the DRS has been excised by recombination between the DRS, by selecting the yeasts not containing the negative marker.

43. A method of integrating a DNA sequence encoding a protein of interest or of inactivating a gene in yeast, comprising:

transforming said yeast with the excision/integration DNA cassette of claim 22;

selecting the yeasts having integrated said cassette by means of said positive marker;

and then, after culturing, selecting yeasts in which the part of the cassette between the DRS has been excised by recombination between the DRS, by selecting the yeasts not containing the negative marker.

44. A method of integrating in a yeast several copies of a DNA sequence encoding a protein of interest or deactivating different copies of a gene of interest, comprising repeating the method of any one of claims 38, 40, 42, 43, 39, or 41, with excision/integration cassettes which contain, for each repeat of the method, different recombinogenic DNA sequences chosen such that each site subject to an integration or being inactivated cannot be the subject of a recombination event with the cassette used subsequently.

45. A yeast obtained by the method of any one of claims 38, 40, 42, 43, 39 or 41, said yeast containing only yeast DNA, wherein the DRS of the cassette are non coding.

* * * * *

UNITED STATES PATENT AND TRADEMARK OFFICE
CERTIFICATE OF CORRECTION

PATENT NO.  : 6,534,315 B1  Page 1 of 1
DATED       : March 18, 2003
INVENTOR(S) : Juergen Bauer, Valerie Nacken and Annie Loiez It is certified that error appears in the above-identified patent and that said Letters Patent is hereby corrected as shown below:

<u>Column 27,</u>
Line 9, please delete the line beginning with "genic:" and insert therefore:
-- genic with the genome of the yeast host strain, --.

Signed and Sealed this

Sixth Day of April, 2004

JON W. DUDAS
*Acting Director of the United States Patent and Trademark Office*